(12) United States Patent
Jensen et al.

(10) Patent No.: US 11,007,028 B2
(45) Date of Patent: May 18, 2021

(54) CROSSED-CYLINDER WRIST MECHANISM WITH TWO DEGREES OF FREEDOM

(71) Applicant: Intuitive Surgical Operations, Inc., Sunnyvale, CA (US)

(72) Inventors: Brian D. Jensen, Orem, UT (US); Larry L. Howell, Orem, UT (US); Spencer P. Magleby, Provo, UT (US); Bryce Edmondson, Provo, UT (US); Jordan Tanner, Provo, UT (US); Clayton Grames, Provo, UT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 38 days.

(21) Appl. No.: 16/290,809

(22) Filed: Mar. 1, 2019

(65) Prior Publication Data
US 2019/0192248 A1 Jun. 27, 2019

Related U.S. Application Data

(63) Continuation of application No. 14/806,331, filed on Jul. 22, 2015, now Pat. No. 10,390,898.
(Continued)

(51) Int. Cl.
*A61B 34/00* (2016.01)
*F16H 55/08* (2006.01)
(Continued)

(52) U.S. Cl.
CPC .............. *A61B 34/71* (2016.02); *A61B 34/30* (2016.02); *B25J 9/104* (2013.01); *B25J 17/0258* (2013.01);
(Continued)

(58) Field of Classification Search
CPC .......... A61B 19/2203; A61B 2034/305; A61B 34/30; A61B 34/71; B25J 17/02;
(Continued)

(56) References Cited

U.S. PATENT DOCUMENTS 1,512,246 A * 10/1924 Slonecker ................. F16D 3/46
464/151
2,453,656 A 11/1948 Bullard
(Continued)

FOREIGN PATENT DOCUMENTS

| CN | 103573921 A | 2/2014 |
|---|---|---|
| DE | 1939518 A1 | 2/1970 |
| WO | WO-03001986 A2 | 1/2003 |

OTHER PUBLICATIONS

CN 103573921 A (Kai Li) Feb. 12, 2014. [online] [retrieved on Jun. 3, 2020. Retrieved from: ProQuest Dialog (Year: 2014).*
(Continued)

*Primary Examiner* — Joseph Brown
(74) *Attorney, Agent, or Firm* — Fish & Richardson P.C.

(57) ABSTRACT

According to an aspect, a device may include a first member, a second member, and a wrist mechanism disposed between the first member and the second member. The wrist mechanism may include a first cylinder portion coupled to the first member, and a second cylinder portion coupled to the second member. The first cylinder portion may be rollably engaged with the second cylinder portion such that movement of the first cylinder portion with respect to the second cylinder portion is configured to cause the first member to move in at least two directions with respect to the second member. The second cylinder portion may be positioned with respect to the first cylinder portion such that a longitudinal axis of the second cylinder portion is orthogonal to a longitudinal axis of the first cylinder portion.

20 Claims, 18 Drawing Sheets

Related U.S. Application Data

(60) Provisional application No. 62/027,508, filed on Jul. 22, 2014.

(51) Int. Cl.

| | | |
|---|---|---|
| *F16H 55/22* | (2006.01) | |
| *B25J 9/10* | (2006.01) | |
| *B25J 17/02* | (2006.01) | |
| *A61B 34/30* | (2016.01) | |
| *A61B 17/00* | (2006.01) | |
| *A61B 17/29* | (2006.01) | |
| *F16H 19/00* | (2006.01) | |

(52) U.S. Cl.
CPC ....... *F16H 55/082* (2013.01); *F16H 55/0813* (2013.01); *F16H 55/22* (2013.01); *A61B 2017/0069* (2013.01); *A61B 2017/2927* (2013.01); *A61B 2034/305* (2016.02); *A61B 2034/306* (2016.02); *F16H 19/001* (2013.01)

(58) Field of Classification Search
CPC .... B25J 17/0258; B25J 17/0275; B25J 9/104; F16H 19/001; F16H 55/0813; F16H 55/082; F16H 55/22; F16H 55/26; F16H 1/12; F16H 2055/173; F16D 3/185; F16D 3/16; F16D 3/18; F16D 3/124
See application file for complete search history.

(56) References Cited

U.S. PATENT DOCUMENTS

| 4,509,932 | A | 4/1985 | Weible |
|---|---|---|---|
| 5,533,418 | A | 7/1996 | Wu et al. |
| 6,146,391 | A | 11/2000 | Cigaina |
| 6,676,684 | B1 | 1/2004 | Morley et al. |
| 7,756,251 | B2 | 7/2010 | Davis et al. |
| 8,137,339 | B2 | 3/2012 | Jinno et al. |
| 8,989,354 | B2 | 3/2015 | Davis et al. |
| 9,027,441 | B2 | 5/2015 | Gewirtz et al. |
| 9,556,947 | B2 | 1/2017 | Hiller et al. |
| 2004/0260334 | A1 | 12/2004 | Braun |
| 2007/0039996 | A1 | 2/2007 | Mather et al. |
| 2011/0106146 | A1 | 5/2011 | Jeong |
| 2011/0118707 | A1 | 5/2011 | Burbank |
| 2012/0239080 | A1 | 9/2012 | Fan |
| 2013/0282023 | A1 | 10/2013 | Burbank et al. |
| 2014/0100558 | A1 | 4/2014 | Schmitz et al. |
| 2015/0128734 | A1 | 5/2015 | Hong |
| 2016/0022365 | A1 | 1/2016 | Jensen et al. |

OTHER PUBLICATIONS

Senapati S., et al., "Surgical techniques: Robot-assisted laparoscopic myomectomy with the da Vinci surgical system," Journal of Robotic Surgery, 2007, vol. 1(1), pp. 69-74.

Nai T.Y., et al., "Steerable Mechanical Joint for High Load Transmission in Minimally Invasive Instruments," Journal of Medical Devices, 2011, vol. 5(034503), 6 pages.

Halverson P.A., et al., "Tension-Based Multi-Stable Compliant Rolling-Contact Elements", Mechanism and Machine Theory, 2010, vol. 45(2), pp. 147-156.

International Preliminary Report on Patentability for Application No. PCT/US2015/041584, dated Feb. 2, 2017, 11 pages.

Toone N.C., et al., "Investigation of Unique Carbon Nanotube Cell Restraint Compliant Mechanisms," Mechanics-Based Design of Structures and Machines, 2014, vol. 42(3), pp. 343-354.

International Search Report and Written Opinion for Application No. PCT/US2015/041584, dated Oct. 27, 2015, 17 pages.

Jelinek F., et al., "DragonFlex-Smart Steerable Laparoscopic Instrument," Journal of Medical Devices, Mar. 2013, vol. 7(020911), 2 pages.

Zhao B., et al., "Decoupled Cable-Driven Grasper Design Based on Planetary Gear Theory," J. Medical Devices, 2013, vol. 7(020918), 3 pages.

Zoppi M., et al., "Design of a Microrobotic Wrist for Needle Laparoscopic Surgery," J. Mechanical Design, 2008, vol. 130(102306), 8 pages.

* cited by examiner

CROSSED-CYLINDER WRIST MECHANISM WITH TWO DEGREES OF FREEDOM

CROSS-REFERENCE TO RELATED APPLICATION

This application is a continuation of U.S. patent application Ser. No. 14/806,331, entitled "Crossed-Cylinder Wrist Mechanism with Two Degrees of Freedom", filed on Jul. 22, 2015, which claims priority to U.S. Patent Application No. 62/027,508, filed on Jul. 22, 2014, entitled "Crossed-Cylinder Wrist Mechanism with Two Degrees of Freedom", all of which are incorporated by reference in their entirety.

TECHNICAL FIELD

This disclosure relates generally to devices having a crossed-cylinder wrist mechanism with two degrees of freedom and methods of manufacturing the same, and particularly surgical devices having the wrist mechanism with two degrees of freedom.

BACKGROUND

Minimally Invasive Surgery (MIS) is a growing field including both laparoscopic and robotic operations. Surgeons and engineers are making continual efforts to mitigate the negative effects of procedures on patients. Reducing the size of the surgical instruments is one effective method pursued in this effort. In some examples, surgical instruments may include wrist mechanisms. Also, other areas such as robotics may use wrist mechanisms. For instance, wrist mechanisms are commonly used in a wide variety of grasping, cutting, and manipulating operations. In some examples, wrist mechanisms may allow control of an angle of a tool with respect to a mounting shaft. Typically, the wrist mechanism is placed at the end of the shaft, before the tool (e.g., cutter or grasper) to improve the dexterity of the tool. In some conventional examples, the wrist mechanism may be one or more hinges that permit the tool to move with respect to the shaft with two degrees of freedom. However, in some examples, these conventional wrist mechanisms may produce large swept volumes when they move due to the distance between centers of rotation for the two degrees of freedom. Also, due to manufacturing constraints and the increased importance of friction at small scales, it may be challenging to produce a small-scale wrist mechanism that is relatively easy to manufacture and assemble.

SUMMARY

According to an aspect, a device may include a first member, a second member, and a wrist mechanism disposed between the first member and the second member. The wrist mechanism may include a first cylinder portion coupled to the first member, and a second cylinder portion coupled to the second member. The first cylinder portion may be rollably engaged with the second cylinder portion such that movement of the first cylinder portion with respect to the second cylinder portion is configured to cause the first member to move in at least two directions with respect to the second member. The second cylinder portion may be positioned with respect to the first cylinder portion such that a longitudinal axis of the second cylinder portion is orthogonal to a longitudinal axis of the first cylinder portion.

In some examples, the device may include one or more of the following features (or any combination thereof). Each of the first cylinder portion and the second cylinder portion may define a rounded surface portion, and the rounded surface portion may define a plurality of gear teeth. Each gear tooth of the plurality of gear teeth may include a first gear profile and a second gear profile, where the second gear profile is different than the first gear profile. The plurality of gear teeth may be arranged into a plurality of rows of gear teeth including a first row of gear teeth and a second row of gear teeth, where the second row of gear teeth is staggered from the first row of gear teeth. The wrist mechanism may include a coupling member configured to couple the first cylinder portion to the second cylinder portion to keep the first cylinder portion in contact with the second cylinder portion but permit the first cylinder portion to roll with respect to the second cylinder portion. The coupling member may include a plurality of activation members coupled to the first cylinder portion. The first member may include a tool member, and the second member may include a shaft. The distance between the longitudinal axis of the first cylinder portion and the longitudinal axis of the second cylinder portion may be within a range of 1-4 millimeters. The first cylinder portion may be configured to move in a direction parallel to the longitudinal axis of the second cylinder portion, and move in a direction around the longitudinal axis of the second cylinder portion. The first cylinder portion may be configured to roll around the longitudinal axis of the first cylinder portion such that the first cylinder portion moves along at least a portion of a surface length of the second cylinder portion in a direction parallel to the longitudinal axis of the second cylinder portion, and the first cylinder portion may be configured to move along a surface arc of the second cylinder portion such that the first cylinder portion moves around the longitudinal axis of the second cylinder portion. The at least two directions may include a first direction and a second direction, the second direction being orthogonal to the first direction. Each of the first cylinder portion and the second cylinder portion may include a plurality of stacked carbon nanotube composite sheets. The wrist mechanism may have a diameter of 5 millimeters or less than 5 millimeters.

According to an aspect, a medical device may include a tool member, a shaft, and a wrist mechanism disposed between the tool member and the shaft. The wrist mechanism may include a first cylinder portion coupled to the shaft, and a second cylinder portion coupled to the tool member. The second cylinder portion may be positioned with respect to the first cylinder portion such that a longitudinal axis of the second cylinder portion is orthogonal to a longitudinal axis of the first cylinder portion. Each of the first cylinder portion and the second cylinder portion may define a rounded surface portion, and the rounded surface portion may define a plurality of rows of gear teeth.

The medical device may include one or more of the above or below features (or any combination thereof). The second cylinder portion may define a platform that is devoid of gear teeth. The medical device may include a plurality of actuation members coupled to corner portions of the platform. When a force applied to one or more of the plurality of actuation members, the tool member may be configured to move in at least two directions. The plurality of rows of gear teeth may include a first row of gear teeth, a second row of gear teeth adjacent to the first row, and a third row of gear teeth adjacent to the second row, where the gear teeth of the second row is offset from the gear teeth of the first row, and the gear teeth of the first row is aligned with the gear teeth of the third row. Each gear tooth of the plurality of rows of gear teeth may include an involute profile and a rack profile.

According to an aspect, a wrist mechanism may include a first cylinder portion, and a second cylinder portion rollably engaged with the first cylinder portion. Each of the first cylinder portion and the second cylinder portion may define a rounded surface portion, and the rounded surface portion may define a plurality of rows of gear teeth. The plurality of rows of gear teeth may include a first row of gear teeth, and a second row of gear teeth adjacent to the first row, where the gear teeth of the second row is offset from the gear teeth of the first row.

In some examples, the wrist mechanism may include the above or below features (or any combination thereof). Each gear tooth of the plurality of rows of gear teeth may include an involute profile and a rack profile. The second cylinder portion may be positioned with respect to the first cylinder portion such that a longitudinal axis of the second cylinder portion is orthogonal to a longitudinal axis of the first cylinder portion.

DETAILED DESCRIPTION

Figure 1:
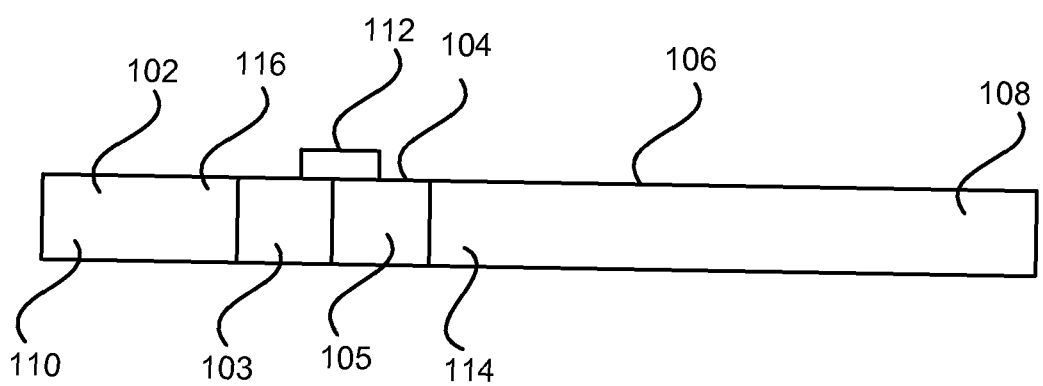
FIG. 1 illustrates a device having a crossed-cylinder wrist mechanism with two degrees of freedom according to an aspect.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a person, such as a surgeon, a physician, a nurse, a doctor, a technician, and the like who may perform the procedure and operate the medical device as described in the present invention, or the operator may be a teleoperated or robotic manipulator technology that likewise operates the medical device. The term proximal refers to an area or portion that is closer or closest to the operator during a surgical procedure. The term distal refers to an area or portion that is farther or farthest from the operator.

The devices discussed herein provide a two-degree-of-freedom (2-DOF) wrist mechanism having a first cylinder portion rollably or rotatably engaged with a second cylinder portion such that the first cylinder portion rolls with respect to the second cylinder portion in a first direction, and/or the second cylinder portion rolls with respect to the first cylinder portion in a second direction that is different from the first direction. In some examples, the first cylinder portion and the second cylinder portion may roll or rotate with respect to each other such that they are positively engaged and have no slip (or substantially no slip). In some examples, each of the first cylinder portion and the second cylinder portion is a section (e.g., one half) of a right circular cylinder, and each of the first and second cylinder portions has an associated longitudinal axis that is defined along the length (between the ends) of the cylinder portion. The two half cylinders may contact each other in a manner that the longitudinal axis of the first cylinder portion is orthogonal to the longitudinal axis of the second cylinder portion, thereby producing a crossed-cylinder wrist mechanism.

In some examples, the first cylinder portion remains stationary in space (e.g., the first cylinder portion is coupled to a fixed support, such as a surgical instrument shaft) while the second cylinder portion moves in two ways with reference to the first cylinder portion. First, the second cylinder portion may move by rolling around its own longitudinal axis so that the second cylinder portion moves along a surface length of the first cylinder in a direction parallel to the first cylinder's longitudinal axis. Second, the second cylinder portion may move along a circular surface arc of the first cylinder portion so that the second cylinder portion moves (orbits) around the first cylinder's longitudinal axis. In other examples, both the first cylinder portion and the second cylinder portion are free to move with reference to each other, and so each cylinder portion may move in these two ways with reference to the other cylinder portion. From these examples, it can be seen that the two cylinder portions act together to form a two degrees-of-freedom rotational joint so that the orientation of an object coupled to the second cylinder portion may be changed with two rotational degrees of freedom with reference to an object coupled to the first cylinder portion. In some examples, the crossed-cylinder wrist mechanism may be capable of rotating up to 90° in either of the two directions (2-DOF) (e.g., the first cylinder portion may rotate up to 90° along the second cylinder portion's axis, and around the second cylinder portion's circumference).

The crossed-cylinder wrist mechanism may improve dexterity and manipulation of small-scale tools, including cutters, graspers, and other robotic tools. In some examples, the wrist mechanism may include a coupling member configured to couple the first cylinder portion to the second cylinder portion in order to keep the cylinder portions together but permit the first cylinder portion to roll with respect to the second cylinder portion (and/or vice versa). In some examples, the coupling member may include wires or cables. Also, the wires or cables may operate as an actuator mechanism to allow the operator to control the movement of the cylinder portions. In some examples, four cables are attached to the platform of the second cylinder portion, and forces applied to one or more of these cables cause the second cylinder portion to roll or rotate in at least two directions.

In some examples, the cylinder portions' motion may be restricted to two directions (e.g., a first direction and a second direction orthogonal to the first direction). For example, to limit the cylinder portions' motion, gear teeth may be disposed on the outer surfaces of the cylinder portions to allow rolling motion in only the first direction and the second direction. In other examples, the rolling motions of the cylinder portions are not limited to two directions but rather may roll in more than two directions.

The wrist mechanism may be a small-scale wrist mechanism. For example, the small-scale wrist mechanism may have dimensions on the order of 1-5 mm (e.g., the diameter of the wrist mechanism as a whole, or a distance between the longitudinal axes of the two cylinder portions is on the order of 1-5 mm, to that the wrist mechanism can be effectively used for minimally invasive surgery). In some examples, the wrist mechanism may be substantially around 3 mm. In some examples, the wrist mechanism may be substantially around 4 mm. For instance, when instruments approach 5 mm in diameter (or less), they reach a threshold where the entry incisions can be small enough such that no scar is left on the patient. Laparoscopic instruments on this scale exist but typically lack wrist mechanisms (or wrist articulation) and only have one degree of freedom. Robotic surgical instruments can achieve a high level of dexterity but often requires a greater diameter (e.g., above 5 mm in diameter). Typically, smaller diameter robotic instruments employ what can be referred to as a "snake wrist" architecture that comprises a continuum flexure, a plurality of individual flexures, or a plurality of revolute or rolling joins with parallel rotation axes and limited individual-joint ranges of motion. The plurality of joints or flexures in the snake wrist architectures combine to give a large overall range of motion but this typically results in large swept volumes.

The design of the wrist mechanism may provide minimal rubbing or contacting parts, which may result in relatively low friction while preventing slip. In some examples, the surfaces of the cylinder portions may be populated with gearing that enables the two cylinder portions of the joint to roll in two directions while preventing slip. For example, involute gear profiles may be used along the curvature of the cylinder portions, and a rack profile may be used along the axis of the cylinder portions. In an involute gear, the profiles of the teeth are involutes of a circle. The involute of a circle is the spiraling curve traced by the end of an imaginary taut string unwinding itself from that stationary circle called the base circle. Irrespective of whether a gear is spur or helical, in every plane of the involute gears, the contact between a pair of gear teeth occurs at a single instantaneous point where two involutes of the same spiral hand meet. Rotation of the gear causes the location of the contact point to move across the respective tooth surfaces.

Additionally, every other row of gearing may be offset by half the pitch (e.g., the circular pitch) of the involute gearing to increase the number of gear teeth that are engaged at any instant. This concept is discussed in more detail with respect to FIGS. 2, 3A-3B, and 7A-7B. There may be little friction in between the cylinder portions because they roll across one another with relatively little relative motion. Binding, a limiting factor in many small-scale designs caused by friction, is attenuated by this rolling motion. Also, low friction between the cylinder portions may eliminate (e.g., reduce, substantially eliminate) the need for any type of lubricant applied to the wrist mechanism. The gearing between the cylinder portions may ensure that there is effectively no slip (or substantially no slip), leading to a positive engagement design. As a result, there is a predictable relationship between an input motion or force and the resulting output motion or force.

In some examples, the small-scale wrist mechanism may be fabricated using sheets of carbon nanotube composite material. For example, the small-scale wrist mechanism may include stacked sheets of carbon nanotube composite material, where each sheet is lithographically patterned. In some examples, each sheet is individually patterned using photolithography. For assembling the small-scale wrist mechanism, the sheets of carbon nanotube composite material may be stacked according to a stacked configuration. In some examples, the small-scale wrist mechanism may be manufactured using micro laser-sintering (MLS) or other additive methods of manufacturing.

In other examples, the wrist mechanism may be a large-scale wrist mechanism (e.g., large enough so that its dimensions are unusable inside a patient's body, but may be useful for medical device joints outside the body or for joints in other large devices). In some examples, the large-scale wrist mechanism may be fabricated using FDM 3D printing technology. These and other features are further explained with reference to the figures.

FIG. 1 illustrates a device 100 having a crossed-cylinder wrist mechanism 104 with the 2-DOF capability according to an aspect.

In some examples, the device 100 may be a surgical device used during a surgical procedure. In some examples, the device 100 may be used in Minimally Invasive Surgery (MIS) or laparoscopic surgical operations. The device 100 may include a shaft 106 and a tool member 102 (e.g., a surgical end effector), where the wrist mechanism 104 is disposed between and coupled to the shaft 106 and the tool member 102. The shaft 106 may be an elongated circular cross section structure, such as a circular-cross-section tube. In other examples, the shaft 106 may have one or more non-circular-shaped cross section portions. The shaft 106 may include a handle configured to be being gripped by an operator of the device 100.

The tool member 102 may be any type of tool used for a surgical procedure. In some examples, the tool member 102 may be a cutter or scissor. In some examples, the tool member 102 may be a grasper or coupling member configured to grasp or couple another component. In still other examples, the tool member 102 may perform other known surgical functions, such as fusing or stapling tissue, applying clips, cauterizing tissue, and imaging tissue. In other examples, the device 100 having the wrist mechanism 104 may be an implant inserted into the body of the patient. In some examples, the device 100 may couple two body components (e.g., a first member, a second member) with the wrist mechanism 104 in order to provide various ranges of motions. For example, the first member may be any type of structural component capable of being coupled to the first cylinder portion 103, and the second member may be any type of structural component capable of being coupled to the second cylinder portion 105. In some examples, the first member may include the tool member 102, and the second member may include the shaft 106. However, the first member may include another type of component besides the tool member 102, and the second member may include another type of component besides the shaft 106. In some examples, the wrist mechanism 104 may function as an artificial joint. In these examples, the device 100 may not have the tool member 102 and the shaft 106.

The device 100 may have a proximal end portion 108 and a distal end portion 110. The wrist mechanism 104 may be disposed between the proximal end portion 108 and the distal end portion 110. The wrist mechanism 104 may be disposed between the tool member 102 and the shaft 106. For example, the wrist mechanism 104 may be coupled to a distal end portion 114 of the shaft 106, and the wrist mechanism 104 may be coupled to a proximal end portion 116 of the tool member 102.

The wrist mechanism 104 may include a first cylinder portion 103 and a second cylinder portion 105. In some examples, each of the first cylinder portion 103 and the second cylinder portion 105 is one half of a cylinder as described above. For example, a central axis may be defined between the ends of a full cylinder, and the half cylinder may be the bottom or top half of the full cylinder (e.g., the half of the cylinder above the central axis or below the central axis). In some examples, each of the first cylinder portion 103 and the second cylinder portion 105 is a three-dimensional cylindrical gear structure. In some examples, each of the first cylinder portion 103 and the second cylinder portion 105 includes a three-dimensional rounded surface portion with linear edges, and a flat surface or relatively flat surface. The first cylinder portion 103 may be coupled to the proximal end portion 116 of the tool member 102. In some examples, the flat surface of the first cylinder portion 103 is coupled to the proximal end portion 116 of the tool member 102. The second cylinder portion 105 may be coupled to the distal end portion 114 of the shaft 106. In some examples, the flat surface of the second cylinder portion 105 is coupled to the distal end portion 114 of the shaft 106.

The first cylinder portion 103 may be rollably coupled to or engaged with the second cylinder portion 105 such that the first cylinder portion 103 rolls with respect to the second cylinder portion 105 (and/or vice versa) in at least two directions, e.g., a first direction and a second direction. In some examples, the first cylinder portion 103 rolls with respect to the second cylinder portion 105 (and/or vice versa) in only the first and second directions. In some examples, the first direction may be orthogonal to the second direction. In some examples, the first direction is non-orthogonal, but non-parallel to the second direction.

An outer surface of the first cylinder portion 103 may contact an outer surface of the second cylinder portion 105. In some examples, portions of the three-dimensional rounded surface portion of the first cylinder portion 103 may contact portions of the three-dimensional rounded surface portion of the second cylinder portion 105 in a manner that the first cylinder portion 103 rolls with respect to the second cylinder portion 105 (and/or vice versa). Also, the first cylinder portion 103 may be positioned with respect to the second cylinder portion 105 such that the axis of the first cylinder portion 103 is orthogonal to the axis of the second cylinder portion 105. In some examples, because the axis of the first cylinder portion 103 is orthogonal to the axis of the second cylinder portion 105, the first cylinder portion 103 and the second cylinder portion 105 may be considered crossed, thereby producing the crossed-cylinder wrist mechanism. In other words, the cross-cylinder wrist mechanism may be achieved by rotating one of the cylinder portions 103, 105 so that the axes of each cylinder portion 103, 105 are orthogonal to each other.

Each cylinder portion 103, 105 may move parallel to the other cylinder portion's axis as it rolls, thereby providing two rotational degrees of freedom. For example, each cylinder portion 103, 105 may roll along a straight line on the surface of the other cylinder portion 103, 105, thereby allowing two degrees of freedom (e.g., roll in either direction). Further, the outer surfaces of the cylinder portions 103, 105 include gear teeth. The gear teeth on the outer surfaces of the cylinder portions 103, 105 may assist in preventing torsion and shear between the two cylinder portions. Also, the gear teeth may be designed to function in two directions of roll, as further described in FIGS. 2 and 3A-3B.

The wrist mechanism 104 may include a coupling member 112 configured to couple the first cylinder portion 103 to the second cylinder portion 105 in order to keep the cylinder portions 103, 105 together but permit the first cylinder portion 103 to roll with respect to the second cylinder portion 105 (and/or vice versa). In some examples, the coupling member 112 may function as a compressive force between the cylinder portions 103, 105 that ensures that cylinder portions 103, 105 stay in contact with each other. For example, one or more springs may be used to compress cylinder portions 103 and 105 against each other, such as by coupling the one or more springs between the tool member 102 and shaft 106. In some examples, the coupling member 112 may be wires or cables. For example, one or more wires may be coupled to the first cylinder portion 103 and the second cylinder portion 105 in order to keep the cylinder portions 103, 105 together. In these examples, the coupling member 112 may function as part of an activation mechanism, where a force (e.g., pulling) applied to the wires or cables causes the wrist mechanism 104 to move in the first and/or second direction. However, generally, the coupling member 112 may be any type of coupling mechanism that keeps the cylinder portions 103, 105 together but permits the first cylinder portion 103 to roll with respect to the second cylinder portion 105 (and/or vice versa).

Figure 2:
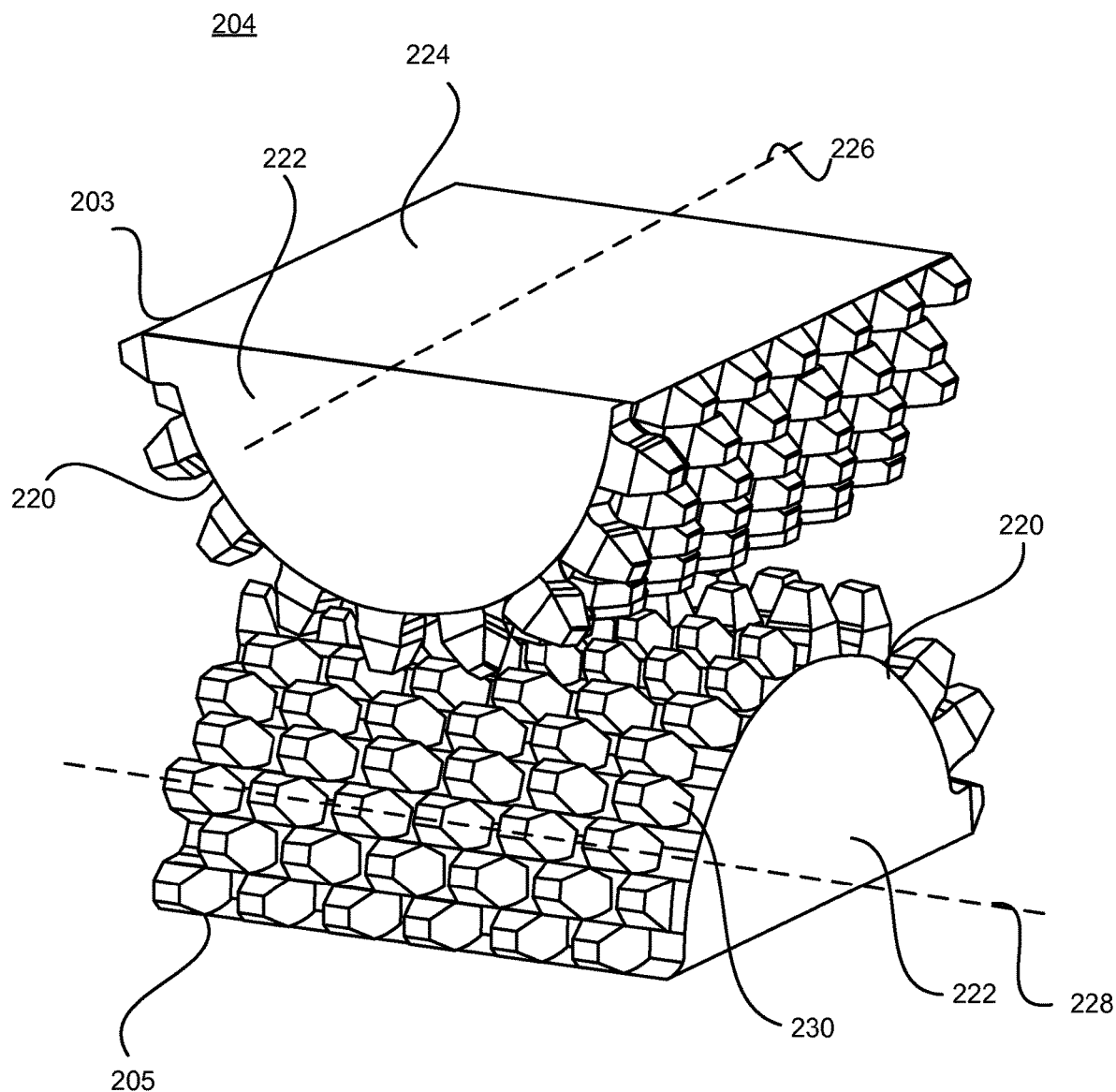
FIG. 2 illustrates a crossed-cylinder wrist mechanism according to an aspect.

FIG. 2 illustrates a crossed-cylinder wrist mechanism 204 according to an aspect. In some examples, the wrist mechanism 204 may include any of the features discussed with reference to the wrist mechanism 104 of FIG. 1 and/or the device 100 of FIG. 1. The wrist mechanism 204 may include a first cylinder portion 203 and a second cylinder portion 205. In some examples, each of the first cylinder portion 203 and the second cylinder portion 205 is one half of a cylinder. In some examples, each of the first cylinder portion 203 and the second cylinder portion 205 is a three-dimensional cylindrical gear structure. In some examples, the first cylinder portion 203 mirrors the second cylinder portion 205 such that they are centered when interfacing with each other. For example, when the first cylinder portion 203 and the second cylinder portion 205 contact each other (e.g., face each other) and the longitudinal axis of the first cylinder portion 203 is parallel to the longitudinal axis of the second cylinder portion 205, the first cylinder portion 203 has a structure that mirrors the structure of the second cylinder portion 205. In some examples, the first cylinder portion 203 has a structure that is the same as the second cylinder portion 205. However, in some examples, the first cylinder portion 203 and the second cylinder portion 205 are not identical. For examples, the first cylinder portion 203 may be different in at least one aspect (e.g., height, length, width, and/or curvature, etc.) than the second cylinder portion 205.

In some examples, each of the first cylinder portion 203 and the second cylinder portion 205 includes a three-dimensional rounded surface portion 220 with edges 222, and a platform 224. The edges 222 may define the ends of the first cylinder portion 203 and the second cylinder portion 205. In some examples, the edges 222 may define a surface that is a semi-circle at each end of a particular cylinder portion. However, the edges 222 may define a surface having other curved and non-curved shapes. The edges 222 may extend between (or be disposed between) the rounded (or curved) surface portion 220 and the platform 224. In some examples, the edges 222 are flat or substantially flat surfaces. In other examples, the edges 222 include one or more curved portions.

In some examples, the platform 224 may define a surface opposite to the rounded surface portion 220 (e.g., the platform 224 may define a surface plane having a width and length). In some examples, the platform 224 may have a uniform width and a uniform length. In other examples, the platform 224 may have multiple different widths and/or multiple different lengths. In some examples, the platform 224 may define a surface that is rectangular. In other examples, the platform 224 may define a surface having a non-rectangular shape. In other examples, the platform 224 includes projections or extensions that extend away from its surface (e.g., include one or more portions having a height or multiple heights). In some examples, the platform 224 may define a recess, hole, or cavity that extend into the cylinder portion. In some examples, the platform 224 of the first cylinder portion 203 may be coupled to the tool member 102 of FIG. 1, and the platform 224 of the second cylinder portion 205 may be coupled to the shaft 106 of FIG. 1. In some examples, the platform 224 and the edges 222 may be devoid of gears.

The three dimensional round surface portion 220 of the first cylinder portion 203 may define a surface having an arc or curve in which the first cylinder portion 203 can roll (e.g., rolling with respect to the first cylinder portion's axis 226). Also, the three dimensional round surface portion 220 of the second cylinder portion 205 may define a surface having an arc or curve in which the first cylinder portion 203 can roll about (e.g., rolling across the second cylinder portion's axis 228 in both directions). The three dimensional round surface portion 220 of the first cylinder portion 203 may face the three dimensional round surface portion 220 of the second cylinder portion 205. The platform 224 of the first cylinder portion 203 and the platform 224 of the second cylinder portion 205 do not face either other (e.g., they face in opposite directions).

The first cylinder portion 203 may be rollably coupled to or engaged with the second cylinder portion 205 such that the first cylinder portion 203 rolls with respect to the second cylinder portion 205 (and/or vice versa) in at least two directions, e.g., a first direction and a second direction. In some examples, the first cylinder portion 203 rolls with respect to the second cylinder portion 205 (and/or vice versa) in only the first and second directions. In some examples, the first direction may be orthogonal to the second direction. In other examples, the first cylinder portion 203 rolls with respect to the second cylinder portion 205 (and/or vice versa) in more than two directions.

An outer surface of the first cylinder portion 203 may contact an outer surface of the second cylinder portion 205. In some examples, portions of the three-dimensional rounded surface portion 220 of the first cylinder portion 203 may contact portions of the three-dimensional rounded surface portion 220 of the second cylinder portion 205 in a manner that the first cylinder portion 203 may roll with respect to the second cylinder portion 205 (and/or vice versa). Also, the first cylinder portion 203 may be positioned with respect to the second cylinder portion 205 such that the axis 226 of the first cylinder portion 203 is orthogonal to the axis 228 of the second cylinder portion 205. In some examples, because the axis 226 of the first cylinder portion 203 is orthogonal to the axis 228 of the second cylinder portion 205, the first cylinder portion 203 and the second cylinder portion 205 may be considered crossed, thereby producing a crossed-cylinder wrist mechanism. In other words, the cross-cylinder wrist mechanism may be achieved by rotating one of the cylinder portions 203, 205 so that the axes 226, 228 of each cylinder portion 203, 205 are orthogonal to each other.

In some examples, the second cylinder portion 205 remains stationary in space (e.g., the second cylinder portion 205 is coupled to a fixed support, such as the shaft 106 of FIG. 1) while the first cylinder portion 203 moves in two ways with reference to the second cylinder portion 205. First, the first cylinder portion 203 may move by rolling around its own axis 226 so that the first cylinder portion 203 moves along a surface length of the three dimensional rounded surface portion 220 of the second cylinder portion 205 in a direction parallel to the second cylinder portion's axis 228. Second, the first cylinder portion 203 may move along the three dimensional rounded surface portion 220 of the second cylinder portion 205 so that the first cylinder portion 203 moves (orbits) around the second cylinder's axis 228. Also, in some examples, the first cylinder portion 203 may move in both of these directions simultaneously. In other examples, both the first cylinder portion 203 and the second cylinder portion 205 are free to move with reference to each other, and so each cylinder portion 203, 205 may move in these two ways with reference to the other cylinder portion. From these examples, the two cylinder portions 203, 205 act (or function) together to form a two degrees-of-freedom rotational joint so that the orientation of an object coupled to the first cylinder portion 203 may be changed with two rotational degrees of freedom with reference to an object coupled to the second cylinder portion 205. In some examples, the crossed-cylinder wrist mechanism may be configured to rotating up to 90° in either of the two directions (2-DOF) (e.g., the first cylinder portion may rotate up to 90° along the second cylinder portion's axis 228, and around the second cylinder portion's circumference). In some examples, when rolling purely along the axis 228 of the second cylinder portion 205, the first cylinder portion 203 rolls like a wheel causing the center of the platform 224 of the first cylinder portion 203 to remain at the same relative elevation. Conversely, when the platform 224 of the first cylinder portion 203 rolls along the curvature of the second cylinder portion 205, it is as if a rectangle is being rolled over a half circle.

The rounded surface portion 220 of the cylinder portions 203, 205 includes gear teeth 230. The gear teeth 230 on the rounded surface portion 220 of the cylinder portions 203, 205 may assist in preventing torsion and shear between the two cylinder portions 203, 205. In some examples, the rounded surface portion 220 on each of the first cylinder portion 203 and the second cylinder portion 205 defines a plurality of rows of gear teeth 230, where each row of gear teeth 230 includes a plurality of gear teeth 230. Each row of gear teeth 230 may extend between the edges 222. In some examples, the number of rows of gear teeth 230 on the first cylinder portion 203 may be the same as the number of rows of gear teeth 230 on the second cylinder portion 205. In other examples, the number of rows of gear teeth 230 on the first cylinder portion 203 may be different than the number of rows of gear teeth 230 on the second cylinder portion 205. In some examples, the number of gear teeth 230 on one or more rows of gear teeth 230 (or all of them) on the first cylinder portion 203 may be the same as the number of gear teeth 230 on one or more rows of gear teeth 230 (or all of them) on the second cylinder portion 205. In other examples, the number of gear teeth 230 on one or more rows of gear teeth 230 (or all of them) on the first cylinder portion 203 may be different as the number of gear teeth 230 on one or more rows of gear teeth 230 (or all of them) on the second cylinder portion 205. With respect to either the first cylinder portion 203 or the second cylinder portion 205 (or both of them), the plurality of rows of gear teeth 230 includes a first row of gear teeth 230 to $N^{th}$ row of gear teeth 230, where N may be any integer greater or equal to 5. In some examples, N may be 18. The plurality of gear teeth 230 in each row may include a first gear tooth to $M^{th}$ gear tooth, where M is greater or equal to 3. In some examples, M may be 6.

In some examples, with respect to each of the first cylinder portion 203 and the second cylinder portion 205, adjacent gear rows may include gear teeth 230 that are offset from one another. In some examples, the offset is one half of the tooth pitch. In some examples, the offset may range from 0 to 1 times the tooth pitch. The offset gear rows may increase the number of gear teeth 230 that are engaged at any instant, thereby reducing slip and decreasing friction. The plurality of rows of gear teeth 230 may include a first row, a second row adjacent to the first row, and a third row adjacent to the second row. The gear teeth 230 of the second row may be offset with respect to the gear teeth 230 of the first row, and the gear teeth 230 of the third row may be offset with respect to the gear teeth 230 of the second row, and so forth for all of the rows. Accordingly, the gear teeth 230 of the first row and the gear teeth 230 of the third row may be arranged in the same manner (e.g., the arrangement of the first row is the same as the arrangement of the third row with the second row being offset from the first and third rows). In some examples, every other row is offset by half of the pitch of a gear tooth, which increases the number of gear teeth 230 that are engaged at any instant.

There may be relatively little friction between the first cylinder portion 203 and the second cylinder portion 205 because they roll across one another with relatively little relative motion. Additionally, the low friction between the first cylinder portion 203 and the second cylinder portion 205 may eliminate (or reduce) the need for any type of lubricant. The gearing between the first cylinder portion 203 and the second cylinder portion 205 ensures that there is effectively no slip, leading to a positive engagement design, and may provide a predictable relationship between an input motion or force and the resulting output motion or force.

Figure 3A:
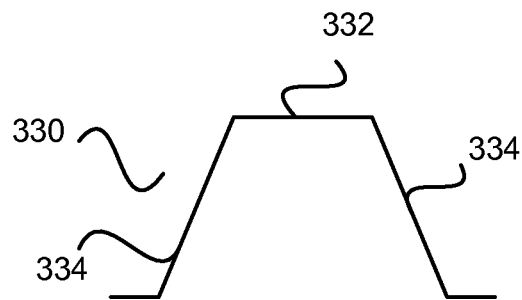
FIG. 3A illustrates a cross-section of a gear tooth in an axial direction according to an aspect.
Figure 3B:
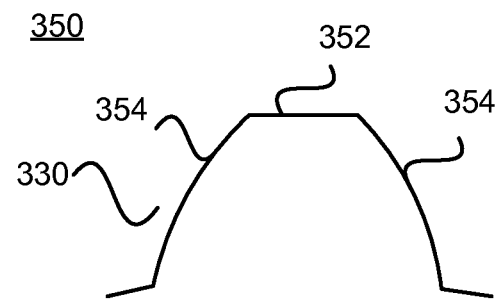
FIG. 3B illustrates a cross-section of the gear tooth in a radial direction according to an aspect.

FIG. 3A illustrates a rack profile 340 of an illustrative gear tooth 330 in an axial direction of a cylinder portion according to an aspect. FIG. 3B illustrates an involute profile 350 of the same gear tooth 330 in a radial direction of the cylinder portion according to an aspect. In other examples, the profile of the gear tooth in the radial direction may be cycloidal. FIGS. 3A and 3B illustrate examples of the gear teeth 230 of FIG. 2.

In some examples, the wrist mechanisms described herein may include two different gear profiles. In some examples, the cross-section of the first cylinder portion 203 and the cross-section of the second cylinder portion 205 are different (e.g., the length, width, curvature, and/or the height are different). As a result, the gearing is designed with two different gear profiles (e.g., an involute profile 350—FIG. 3B, and a rack profile 340—FIG. 3A). In some examples, the same surface (e.g. the rounded surface portion 220) includes both gear profiles. For example, the rounded surface portion 220 of the first cylinder portion 203 includes both the involute profile 350 of FIG. 3B and the rack profile 340 of FIG. 3A, and the rounded surface portion 220 of the second cylinder portion 205 includes the both of the involute profile 350 of FIG. 3B and the rack profile 340 of FIG. 3A.

In some examples, each tooth 330 on the rounded surface portion 220 of the first cylinder portion 203 includes both the involute profile 350 of FIG. 3B (e.g., the involute profile 350 being a cross-section in the radial direction along the curvature of the first cylinder portion 203) and the rack profile 340 of FIG. 3A (e.g., the rack profile 340 being a cross-section in the axial direction along axis 226), and each tooth 330 on the rounded surface portion 220 of the second cylinder portion 205 includes both the involute profile 350 of FIG. 3B (e.g., the involute profile 350 being a cross-section in the radial direction along the curvature of the second cylinder portion 205) and the rack profile 340 of FIG. 3A (e.g., the rack profile 340 being a cross-section in the axial direction along axis 228).

Each gear tooth 330 has a cross-section of a rack tooth in the direction of the cylinder's axis (FIG. 3A). Also, each gear tooth 330 has a cross-section of a normal spur gear tooth (the involute profile 350) in the orthogonal direction (FIG. 3B). In this way, each gear tooth 330 may fit into a gap on the mating cylinder portion 203, 205. Each row of gear teeth 330 may be offset or staggered. For example, by staggering (offsetting) a row of gear teeth 330, the motion is constrained to the 2-DOFs while allowing both cylinder portions 203, 205 to be identical, thereby reducing the number of unique parts. A difference between the gear teeth 330 in the crossed-cylinder mechanism and the normal spur gear teeth is the load they carry. In normal spur gear teeth, the force acts along the line of action, so that the most significant stresses in the tooth are often either shear stresses or bending stresses. However, in the crossed-cylinder wrist mechanism, the gear teeth 330 also support the compressive force acting to keep the cylinder portions 203, 205 in contact.

With respect to the rack profile 340 of FIG. 3A, the gear tooth 330 may include a top portion 332 and angled lateral edges 334. The bottom of the tooth 330 (e.g., the part that is closest to the rounded surface portion 220) is wider than the top of the tooth 330 defined by the top portion 332. The angled lateral edges 334 are disposed at an angle such that the tooth 330 tapers toward the top portion 332. In some examples, the angled lateral edges 334 are angled towards each other. The top portion 332 may connect the angled lateral edges 334. In some examples, the angled lateral edges 334 are linear or straight.

With respect to the involute profile 350 of FIG. 3B, the tooth 330 may define rounded (or curved) lateral edges 354 and a top portion 352 that defines the top of the tooth 330. The bottom of the tooth 330 (e.g., the part that is closest to the rounded surface portion 220) is wider than the top of the tooth 330 defined by the top portion 352. The rounded lateral edges 354 may define a rounded or curved portion on each side of the profile 350. The rounded lateral edges 354 may bulge in a direction away from other. The top portion 352 may connect the rounded lateral edges 354.

Figure 7A:
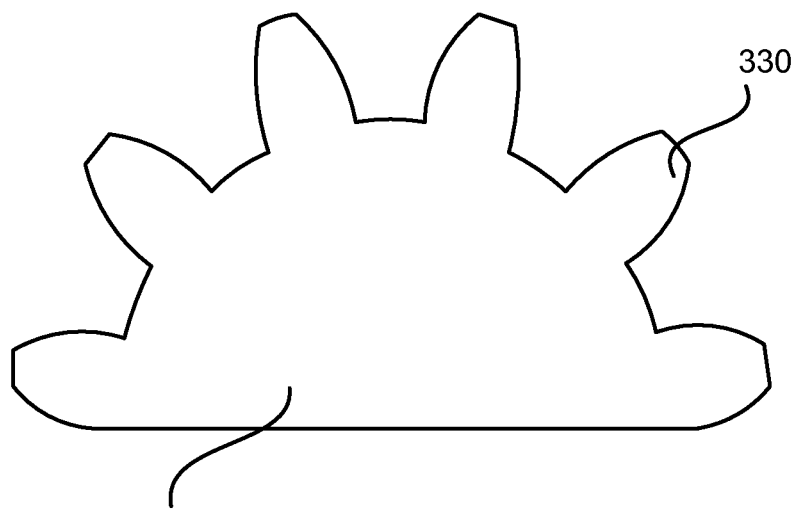
FIG. 7A illustrate an involute profile of a cylinder portion according to an aspect.
Figure 7B:
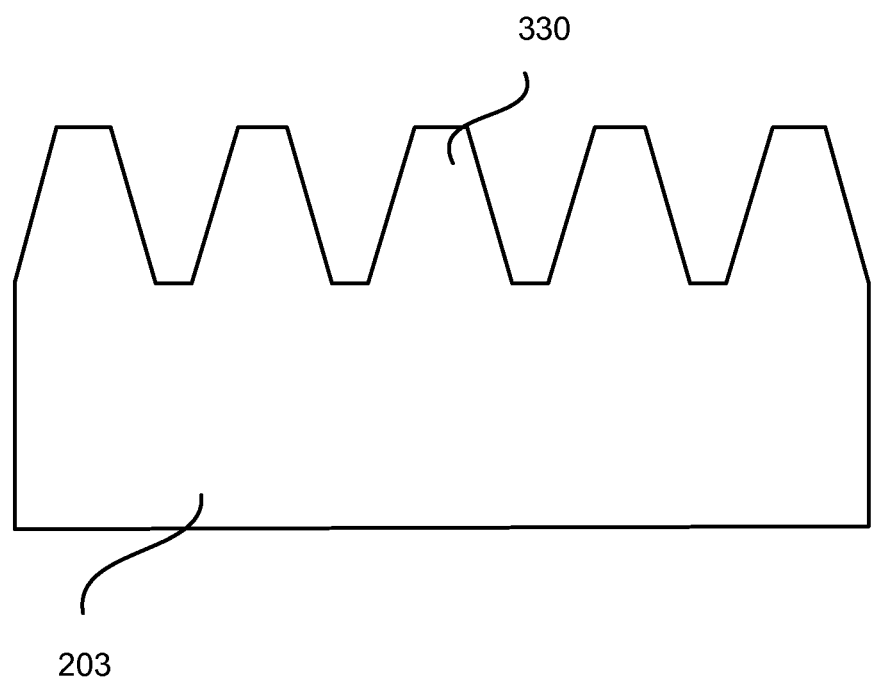
FIG. 7B illustrate a rack profile of the cylinder portion according to an aspect.

FIG. 7A illustrate an involute profile 750 of the first cylinder portion 203 according to another aspect. FIG. 7B illustrate a rack profile 740 of the first cylinder portion 203 according to another aspect. It is noted that the involute profile 750 and the rack profile 740 may be the same for the second cylinder portion 205.

Each tooth 330 incorporates both geometries such that no matter how the joint is displaced (from plus or minus 90 degrees in two orthogonal directions), it will have gear teeth engaged to prevent it from slipping. Thus, each tooth 330 becomes a pseudo-pyramid shape with a trapezoidal rack profile on two sides, and the involute profile on the other sides.

In some examples, the tooth width is half the circular pitch, $$p = \frac{pi}{D_p}, \text{ or } w_t = \frac{p}{2},$$

where $D_p$ is the diametric pitch. Every other row of teeth along the axis of the cylinder is separated by a distance of $w_1$. Additionally, each adjacent row of teeth is rotated by $$\frac{360}{2N}$$

degrees so that when a given tooth is engaged it is surrounded on all sides by mating teeth.

In some examples, the wrist mechanism 204 is configured with a pitch diameter of 3 cm and 18 teeth per full circumference (9 teeth per half-circumference). The designed pressure angle is 20°, and the wrist mechanism 204 has a 3 percent backlash. The wrist mechanism 204 may be assembled by placing the half cylinders together with their axes orthogonal to each other. In one instance, the wrist mechanism was tested by manually rotating the top half-cylinder with respect to the bottom half-cylinder in both degrees of freedom as described above, and the resulting motion was smooth without identifiable interference. In some examples, the wrist mechanism 204 may be able to rotate up to ±90° in both directions (e.g., along the bottom cylinder's axis, and around the bottom cylinder's axis).

Figure 4A:
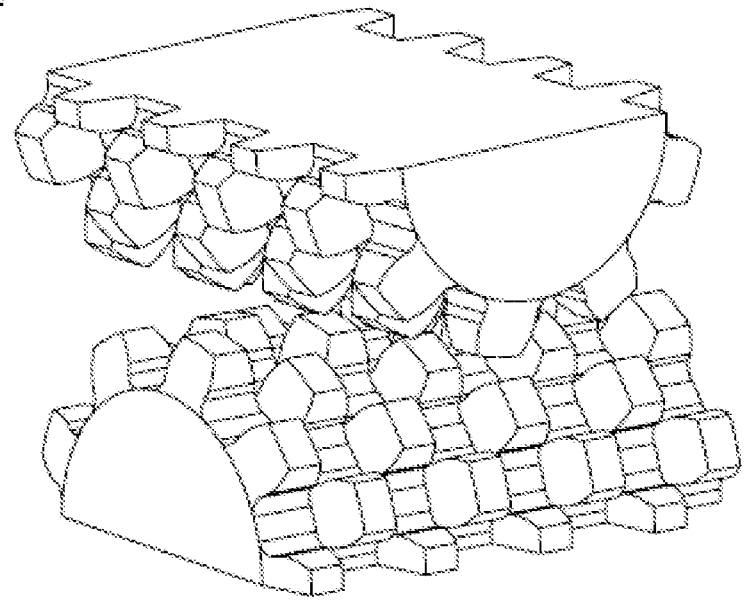
FIG. 4A illustrates the cylinder portions with an angle of 0° with respect to each other according to an aspect.
Figure 4B:
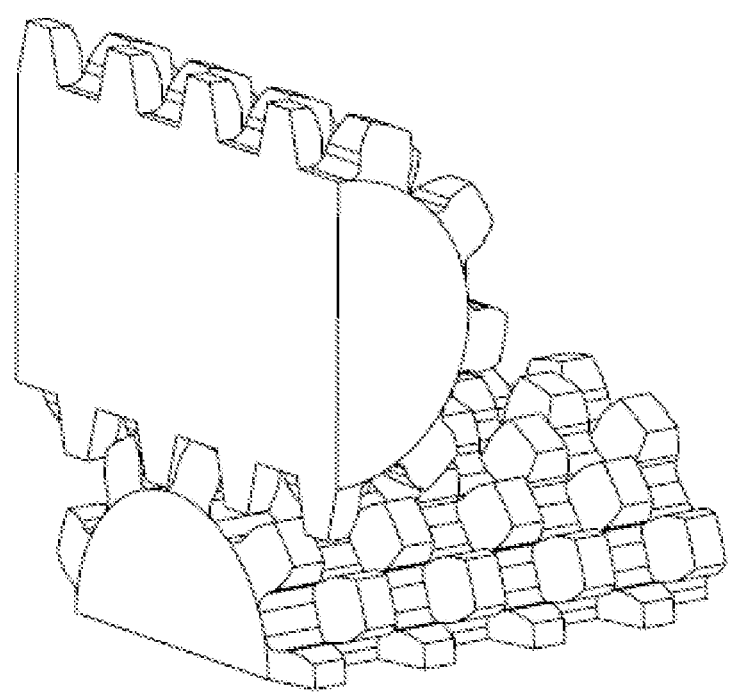
FIG. 4B illustrates the cylinder portions with an angle of 90° with respect to each other according to an aspect.
Figure 4C:
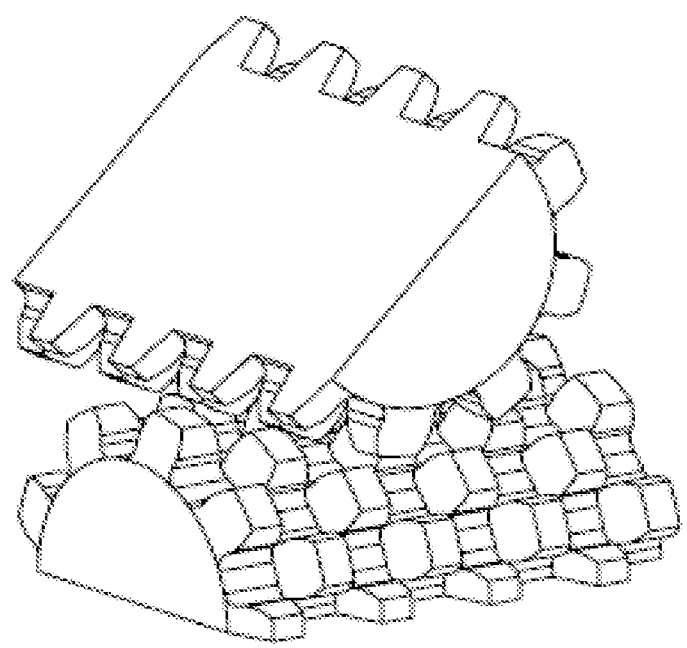
FIG. 4C illustrates the cylinder portions with an angle of 45° with respect to each other according to an aspect.

FIGS. 4A-4C illustrate various views of a wrist mechanism 404 according to an aspect. FIG. 4A illustrate the cylinder portions with an angle of 0° with respect to each other according to an aspect. FIG. 4B illustrates the cylinder portions with an angle of 90° with respect to each other according to an aspect. FIG. 4C illustrates the cylinder portions with an angle of 45° with respect to each other according to an aspect.

FIGS. 5A-5D illustrate various views of a wrist mechanism fabricated by stacking carbon nanotube composite sheets according to an aspect. In some examples, the wrist mechanism may be fabricated using one or more of the techniques described in U.S. patent application Ser. No. 13/453,066 (filed Apr. 23, 2012; titled "Carbon Composite Support Structure") and U.S. patent application Ser. No. 12/239,339 (filed Sep. 26, 2008; titled "X-Ray Radiation Window with Carbon Nanotube Frame"), both of which are incorporated by reference in their entirety.

Figure 5A:
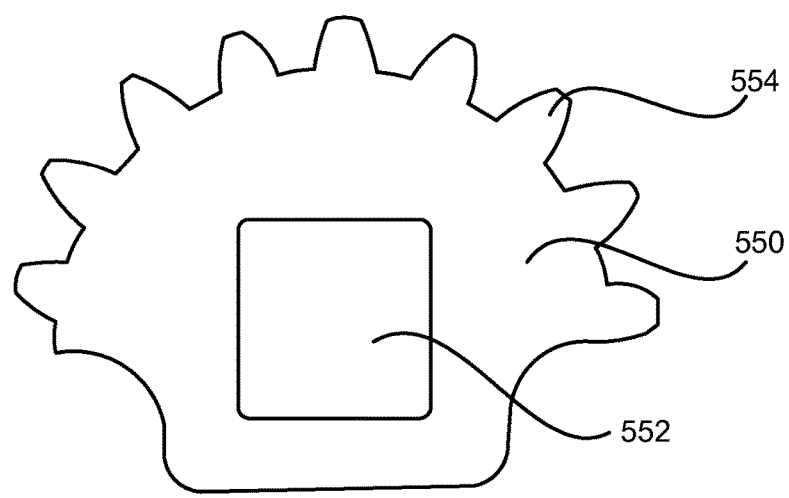
FIG. 5A illustrates a single sheet of material having gear teeth and an opening configured to receive an alignment pin according to an aspect.
Figure 5B:
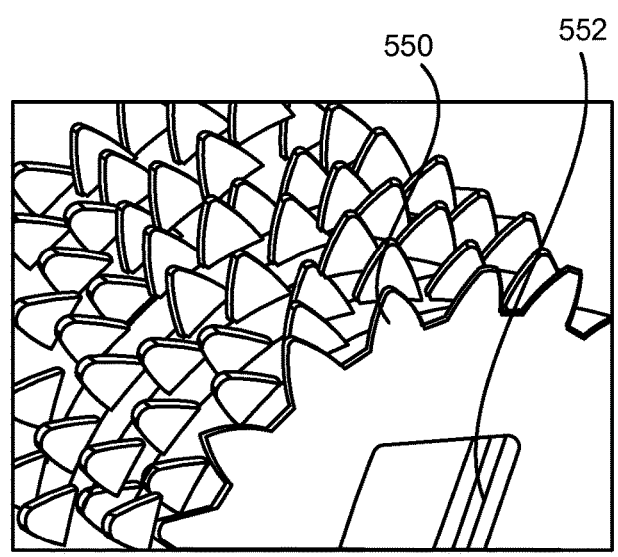
FIG. 5B illustrates a perspective of an assembled cylinder portion having a plurality of sheets in a stacked configuration according to an aspect.
Figure 5C:
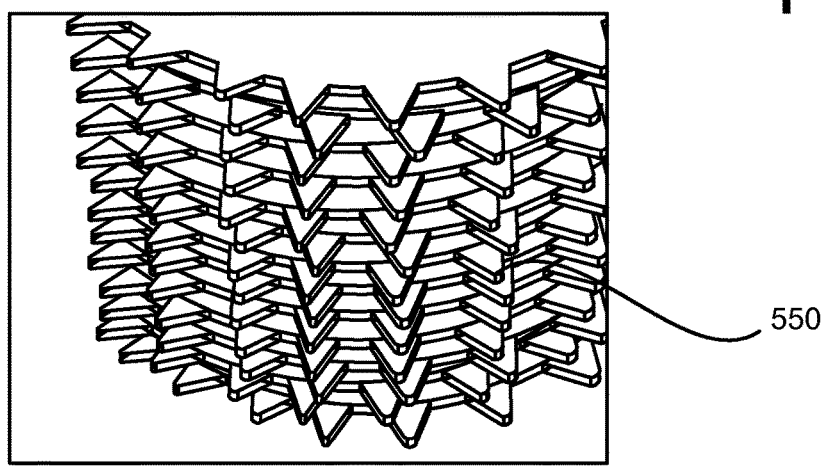
FIG. 5C illustrates another perspective of the assembled cylinder portion having the plurality of sheets in the stacked configuration according to an aspect.
Figure 5D:
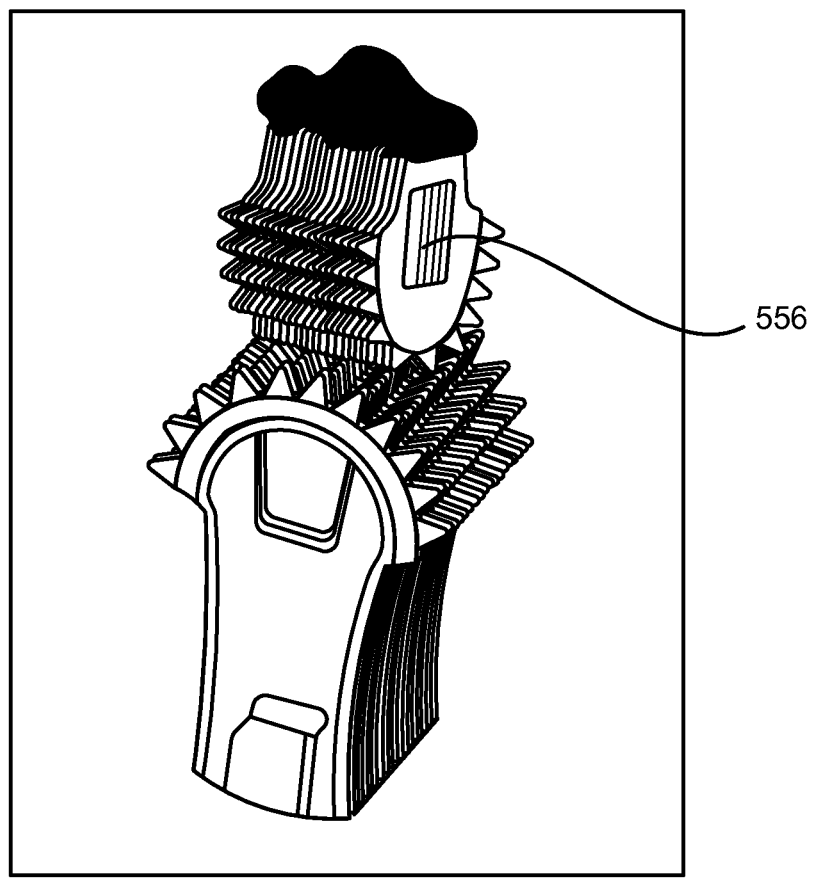
FIG. 5D illustrates an assembled wrist mechanism depicting cylinder portions in a crossed-cylinder configuration according to an aspect.

The wrist mechanism of FIGS. 5A-5D may be considered a small-scale wrist mechanism. In some examples, the wrist mechanism has a maximum dimension (along the diagonal of the half-cylinder's square) within the range of 3 mm to 5 mm. However, the wrist mechanism may have any type of size greater than 5 mm or less than 3 mm. FIG. 5A illustrates a single sheet 550 (e.g., single layer) having gear teeth 554 and an opening 552 configured to receive an alignment pin 556 (see FIG. 5D) according to an aspect. FIG. 5B illustrates a perspective of an assembled cylinder portion having plurality of sheets 550 in a stacked configuration according to an aspect. FIG. 5C illustrates another perspective of the assembled cylinder portion having the plurality of sheets 550 in the stacked configuration according to an aspect. FIG. 5D illustrates an assembled wrist mechanism depicting cylinder portions in a crossed configuration according to an aspect.

Referring to FIGS. 5A-5D, each sheet 550 includes a single layer of carbon nanotube composite material. In some examples, the carbon nanotube composite material includes carbon nanotube forests infiltrated by chemical vapor deposition with carbon. For example, each sheet 550 is lithographically patterned to provide a half-spur gear with alignment features, as shown in FIG. 5A. Thin spacer layers were also produced to give the right spacing between gear teeth 554. Because of the resolution used in the layering process (e.g., each tooth was produced using one layer), the sloped sides of the rack tooth profile were approximated using a rectangular profile. Each cylinder portion was then assembled by stacking multiple sheets 550 in the correct order on the alignment pin 556. The sheets 550 are coupled together using a coupling substance disposed on a surface of each cylinder portion. In some examples, the coupling substance includes an epoxy that is spread along the back surface of each cylinder portion. Although FIG. 5D illustrates adjacent rows of gear teeth being aligned, the gear teeth of the wrist mechanism of FIGS. 5A-5D are actually staggered as shown with respect to the other figures. For example, one sheet 550 with gear teeth is offset with the gear teeth of an adjacent sheet 550 such that a tooth on one sheet 550 located proximately in the center of the teeth gap of the other sheet 550. The result is that the teeth on every other sheet 550 are lined up.

In some examples, the wrist mechanism of FIGS. 5A-5D includes a pitch diameter of 2.03 mm and 18 teeth on the full circumference. However, the wrist mechanism described herein may have a pitch diameter greater or less than 2.03 mm, and the number of teeth on the full circumference of each sheet 550 may be greater or less than 18 teeth. In some examples, the pressure angle is 25°, and the backlash is 5 percent, however these amounts may vary. The wrist mechanism is configured to be actuated by cables attached to the top cylinder portion and that pull on the top cylinder portion to move it in the 2 DOFs as described herein.

The devices and techniques described herein provide a new design for a 2-DOF robotic wrist. The crossed-cylinder wrist mechanism may operate according to a rolling motion while minimizing friction during the operation. Also, the wrist mechanism is designed and configured at relatively small size scales as shown in FIGS. 5A-5D. In some examples, the small size is anywhere between 1 mm and 5 mm-again a size range suitable for minimally-invasive surgical instruments. In some examples, the small-scale wrist mechanism can be fabricated by lithographically patterning sheets of carbon nanotube composite material or lithographically etching sheets of stainless steel (e.g., precipitation hardened 17-4, 17-7, austenitic 300 series, or martensitic 400 series), and then stacking the sheets to form two geared cylinder portions. Also, the wrist mechanism may be fabricated as a large-scale model using FDM 3D printing. Also, the wrist mechanism may be capable of rotating up to 90° in either of two directions (2-DOF). In some examples, the crossed-cylinder wrist mechanism may improve dexterity and manipulation of small-scale tools, including cutters, graspers, and other robotic tools.

Figure 6:
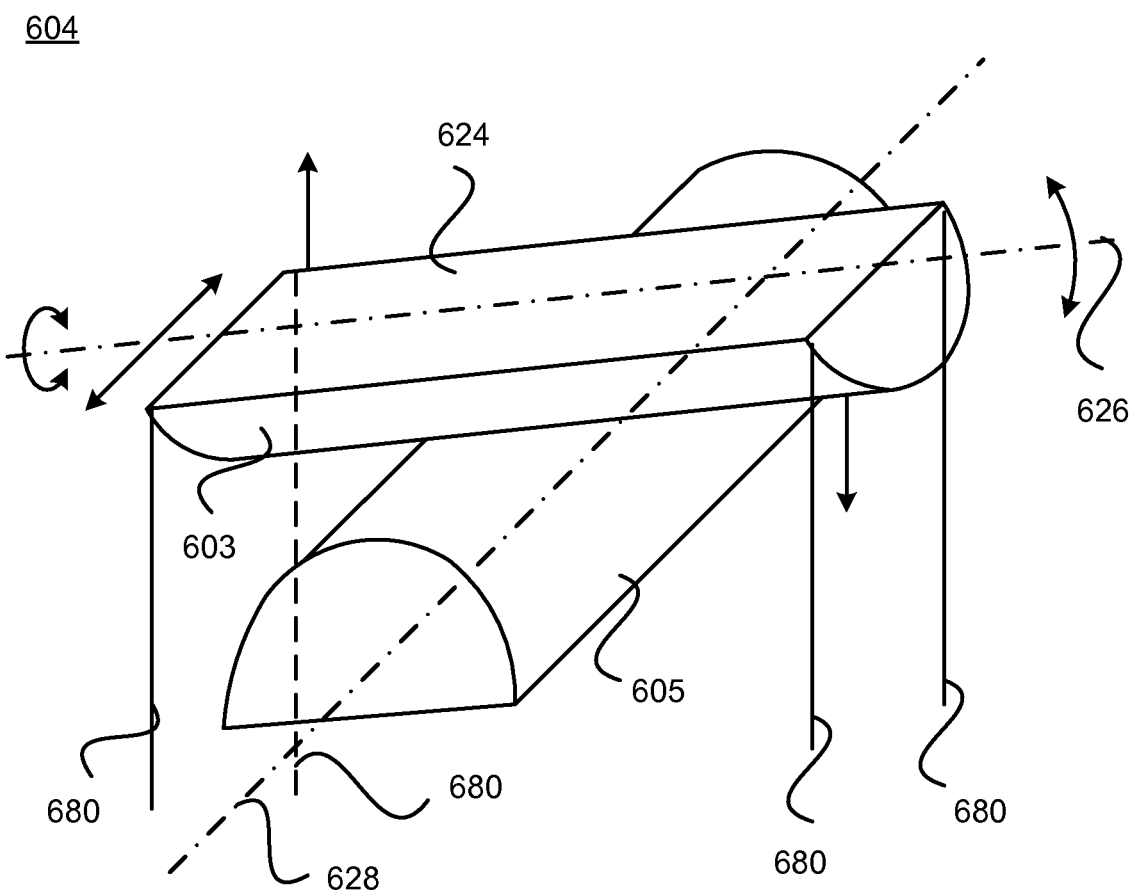
FIG. 6 illustrates a crossed-cylinder wrist mechanism according to an aspect.

FIG. 6 illustrates crossed-cylinder wrist mechanism 604 with the 2-DOF capability according to an aspect. For example, the wrist mechanism 604 may include a first cylinder portion 603 (e.g., top cylinder portion) rollably engaged with a second cylinder portion 605 (e.g., bottom cylinder portion) such that the first cylinder portion 603 moves with respect to the second cylinder portion 605 in a first direction, and/or the second cylinder portion 605 moves with respect to the first cylinder portion 603 in a second direction that is different from the first direction. In some examples, the second cylinder portion 605 may remain stationary, and the first cylinder portion 603 may move in a direction parallel to the second cylinder portion's axis 628, and/or move in a direction around the second cylinder portion's axis 628. In other examples, the first cylinder portion 603 may remain stationary, and the second cylinder portion 605 may move in a direction parallel to the first cylinder portion's axis 626, and/or move in a direction around the first cylinder portion's axis 626. In other examples, both the first cylinder portion 603 and the second cylinder portion 605 are free to move with reference to each other, and so each cylinder portion may move in these two ways with reference to the other cylinder portion.

Also, the first cylinder portion 603 may be coupled to actuation cables 680 in order to control the movement of the first cylinder portion 603 about the second cylinder portion 605. In some examples, an actuation cable 680 is coupled to each corner of a platform 624 of the first cylinder portion 603. The second cylinder portion 605 may be coupled to a shaft, and four actuation cables 680 may be attached at each corner (or each corner portion) of the platform 624 to keep the cylinder portions 603 and 605 in compressive contact during actuation. The actuation cables 680 may be routed between the sides of the joint and the shaft (e.g., through a lumen of the shaft).

Figure 8:
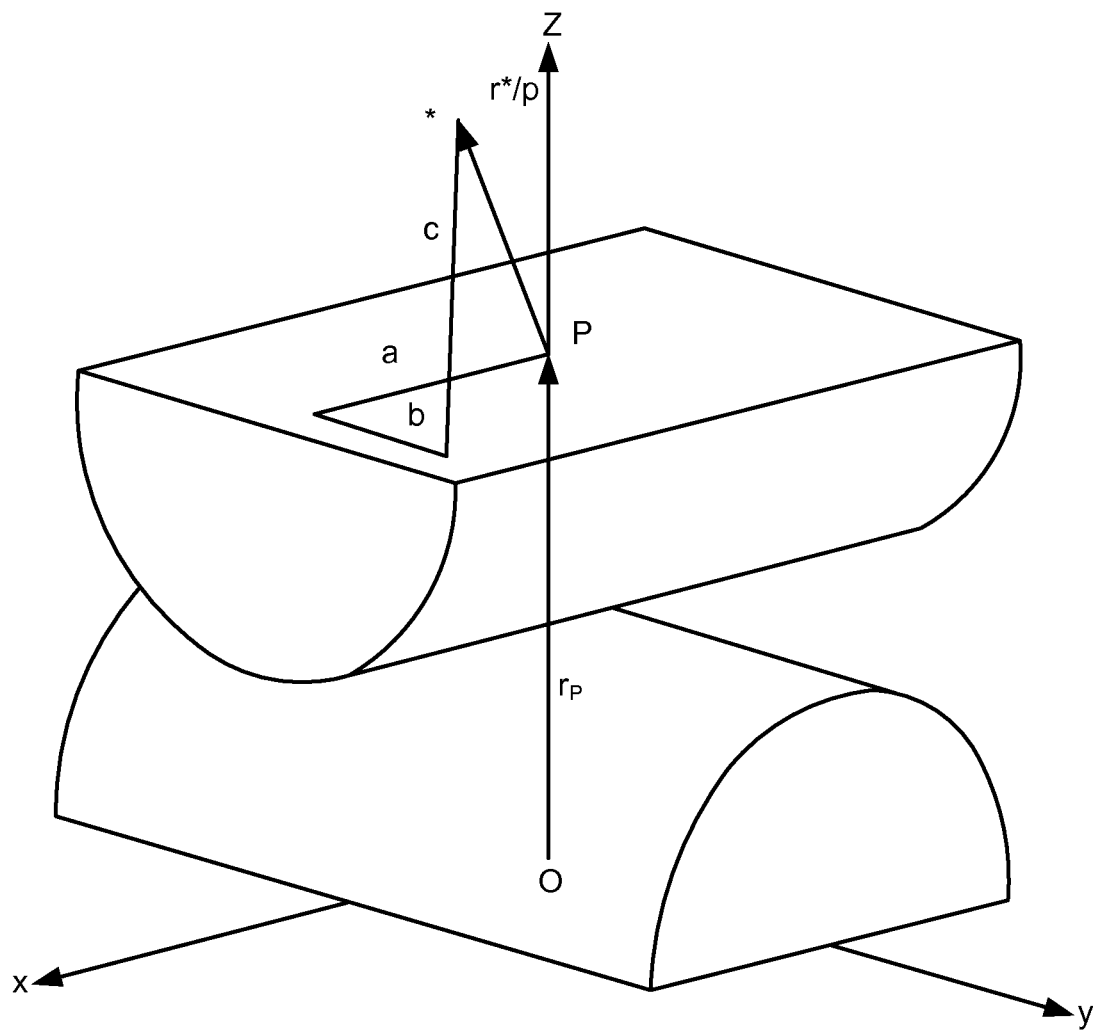
FIG. 8 illustrates an example of cylinder portions and vectors used to describe the kinematics of the wrist mechanism according an aspect.
Figure 9:
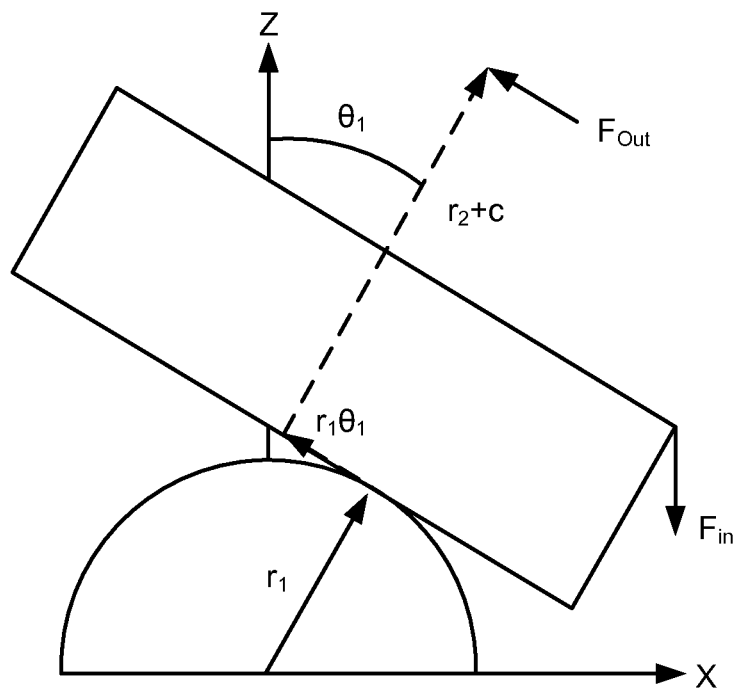
FIG. 9 illustrates a planar view of the wrist mechanism according to an aspect.
Figure 10:
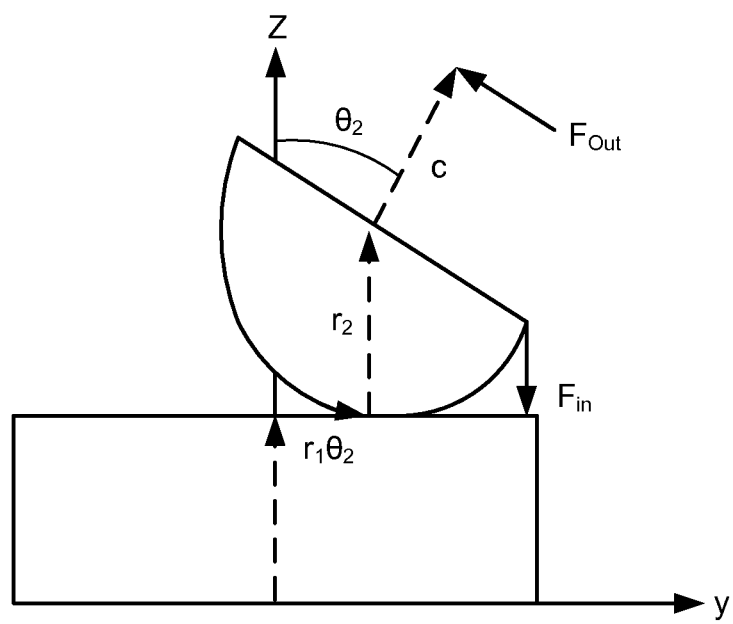
FIG. 10 illustrates a planar view of the wrist mechanism according to another aspect.

FIG. 8 illustrates an example of cylinder portions and the vectors used to describe the kinematics of the crossed cylinders wrist according to an aspect. FIG. 9 illustrates a planar view of the crossed cylinders wrist mechanism according to an aspect. In FIG. 9, the x-z plane is dependent on $\theta_1$. FIG. 10 illustrates a planar view of the crossed cylinders wrist mechanism according to an aspect. In FIG. 10, the y-z plane is dependent on $\theta_2$.

Referring to FIG. 8, the kinematics of the mechanism may be described by two vectors. One vector from the origin O to the center of the platform surface at point P and another from point P to some arbitrary point of interest, as shown in FIG. 8. The first vector was derived by looking at the 2D motion in the x-z and y-z separately. The elevation of the point P only depends on $\theta_1$ (an angular displacement in the x-z plane). This is because when the joint is displaced by $\theta_2$ (the angular displacement in the y-z plane) the point P acts like the center of a wheel and will only translate in the plane. These angles can be seen in FIGS. 9 and 10. Using this information the two separate expressions can be joined to define the vector in Eq. 1 below:

$$r_P = [(r_1+r_2)\sin\theta_1 - r_1\theta_1\cos\theta_1]\hat{i} - r_2\theta_2\hat{j} + [(r_1+r_2)\cos\theta_1 + r_1\theta_1\sin\theta_1]\hat{k}$$

Figure 11:
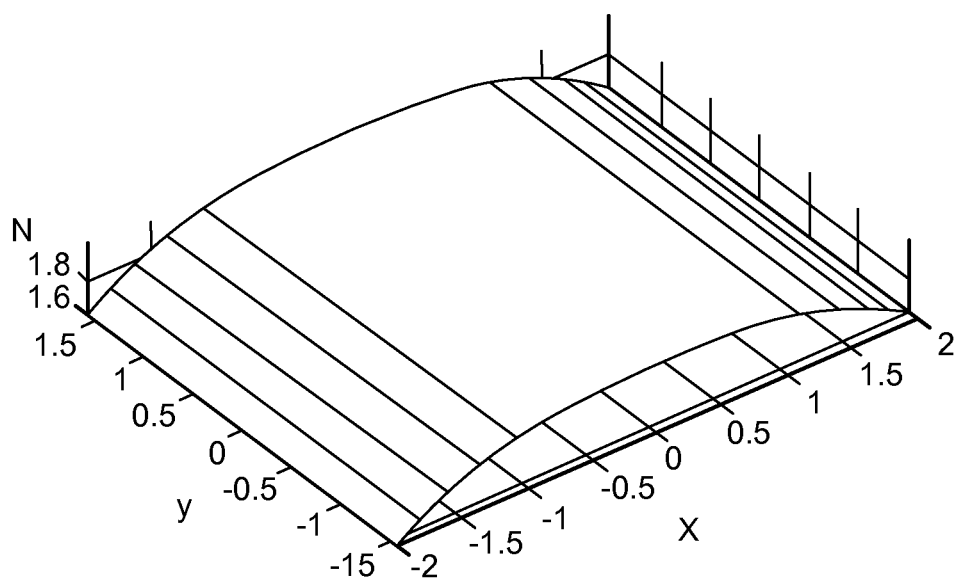
FIG. 11 illustrates a graph of a surface of the wrist mechanism traced by a point according to an aspect.
Figure 12:
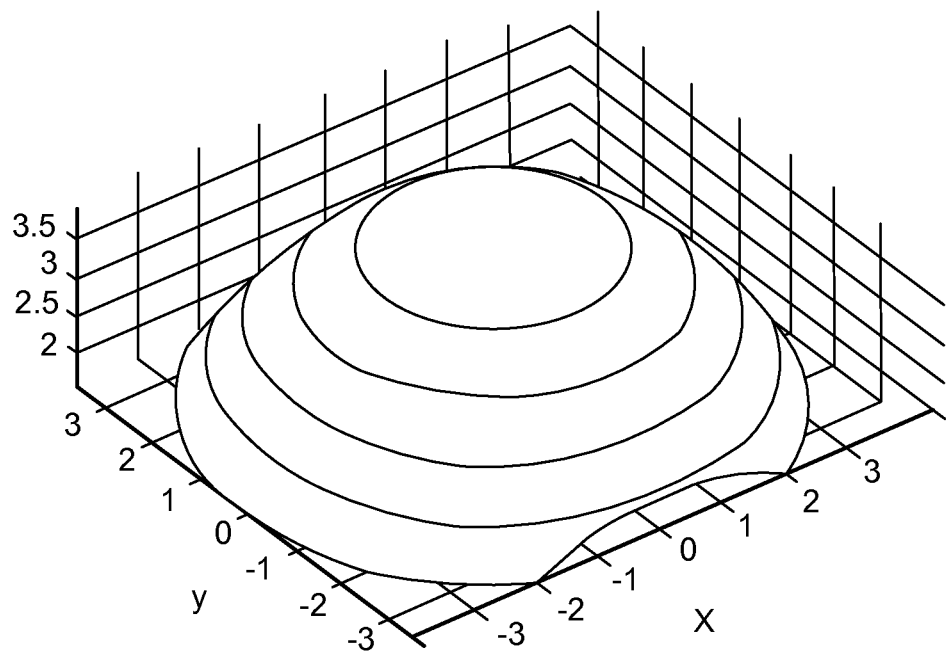
FIG. 12 illustrates a graph of a surface of the wrist mechanism traced by another point according to an aspect.

This motion of this point traces out a surface that can be seen FIG. 11. FIG. 11 illustrates a surface traced by point P as $\theta_1$ and $\theta_2$ vary from plus and minus 90 degrees. Also, FIG. 12 illustrates a surface traced by point* (a and b=0, c=1) as $\theta_1$ and $\theta_2$ vary from plus and minus 90 degrees.

The second vector can be described using a body-fixed frame with its origin attached to point P. The vector from P to * in the new coordinate frame is Eq. 2:

$$r'_{*/P} = a\,\hat{i}' + b\,\hat{j}' + c\,\hat{k}'$$

When the joint is un-deflected, or $\theta_1 = \theta_2 = 0$, the rotating frame is lined up with the global coordinate system. For any given position, the rotating frame can be thought to go through some initial rotation about the y axis followed by another rotation about its new x axis. These rotations correspond to $\theta_1$ and $\theta_2$ respectively. Therefore, in order to transform $r'_{*/P}$ into the global coordinate frame, two simple rotations matrices (Eqs. 3 and 4) can be multiplied together to express a single rotation matrix (Eq. 5) transforming vectors from the global coordinate frame into the rotating frame.

$$[R_y] = \begin{bmatrix} \cos\theta_1 & 0 & -\sin\theta_1 \\ 0 & 1 & 0 \\ \sin\theta_1 & 0 & \cos\theta_1 \end{bmatrix}$$

$$[R_x] = \begin{bmatrix} 1 & 0 & 0 \\ 0 & \cos\theta_2 & \sin\theta_2 \\ 0 & -\sin\theta_2 & \cos\theta_2 \end{bmatrix}$$

$$[R] = [R_x][R_y] = \begin{bmatrix} \cos\theta_1 & 0 & -\sin\theta_1 \\ \sin\theta_1\cos\theta_2 & \cos\theta_1 & \cos\theta_1\sin\theta_2 \\ \sin\theta_1\cos\theta_2 & -\sin\theta_2 & \cos\theta_1\cos\theta_2 \end{bmatrix}$$

Conversely, the transformation from the rotation frame back into the global coordinate system can be achieved by simply using the transposed rotation matrix (Eq. 6) to modify a vector of interest.

$$[R]^T = \begin{bmatrix} \cos\theta_1 & \sin\theta_1\sin\theta_2 & \sin\theta_1\cos\theta_2 \\ 0 & \cos\theta_1 & -\sin\theta_2 \\ -\sin\theta_1 & \cos\theta_1\sin\theta_2 & \cos\theta_1\cos\theta_2 \end{bmatrix}$$

Using this method, $r\cdot_1 P$ can be transformed into the global coordinate system by the expression $r\cdot_1 P = Rr\cdot_1 P$. This yields Eq. 7:

$$r_{*/P} = (a\cos\theta_1 + b\sin\theta_1\sin\theta_2 + c\sin\theta_1\cos\theta_2)\hat{i} + (b\cos\theta_2 - c\sin\theta_2)\hat{j} + (-a\sin\theta_1 + b\cos\theta_1\sin\theta_2 + c\cos\theta_2\cos\theta_2)\hat{k}$$

The total vector from the origin to point * is now a matter of vector addition, where $r = rP + r\cdot_1 P$. Eq. 8:

$$r* = [r_1 + r_2(\sin\theta_1 + (a - r_1\theta_1)\cos\theta_1 + b\sin\theta_1\sin\theta_2 + c\sin\theta_1\cos\theta_2]\hat{i} + [b\cos\theta_2 - c\sin\theta_2 - r_2\theta_2]\hat{j} + [r_1 + r_2)\cos\theta_1 + (r_1\theta_1 - a)\sin\theta_1 + b\cos\theta_1\sin\theta_2 + c\cos\theta_2\cos\theta_2]\hat{k}$$

This expression can generate surfaces traced by any point fixed to the platform. For example, if some sort of gripper (of length equal to 1 radius) were fixed to the platform, it would trace out a surface with the same shape shown in FIG. 12. The somewhat elliptical surface is a product of the non-constant center of rotation. As the distance above the surface of the platform increases the surface will take on a more spherical shape. While the effective radius is increasing the change in center of rotation stays constant.

The wrist mechanism may have one or more mechanical advantages. For example, the expression given in Eq. 8 can be modified to give the location of any point of interest fixed to the platform. This can be useful when determining the relationship between input and output forces. The crossed cylinders wrist has uncoupled motion in two directions. To simplify initial calculations, the mechanical advantage was initially derived for two planar cases.

The principle of virtual work can be applied to a simplified planar model of the crossed cylinders wrist to develop an expression for the mechanical advantage. FIGS. 9 and 10 show the parameters used in the following derivation. An input force (Eq. 9) applied at the top right corner, or a magnitude of a away from point P is assumed to, in some implementations, act vertically downward.

$$F_{in} = -F_{in}\hat{k}$$

An opposing follower force, modeling some output force, is applied a distance c above the center of the upper half of the joint as expressed in Eq. 10:

$$F_{out} = F_{out}(-\cos\theta_1\hat{i} + \sin\theta_1\hat{k})$$

The position vectors to the input and output forces are expressed in Eqs. 11 and 12 respectfully.

$$r_{in} = [(r_1+r_2)\sin\theta_1 + (a-r_1\theta_1)\cos\theta_1]\hat{i} + [(r_1+r_2)\cos\theta_1 + (r_1\theta_1-a)\sin\theta_1]\hat{k}$$

$$r_{out} = [(r_1+r_2+c)\sin\theta_1 + r_1\theta_1\cos\theta_1]\hat{i} + [(r_1+r_2+c)\cos\theta_1 + r_1\theta_1\sin\theta_1]\hat{k}$$

Taking the derivatives of the position vectors with respect to the generalized coordinate and simplifying the virtual displacements become Eqs. 13 and 14:

$$\delta r_{in}\{[r_2\cos\theta_1 - a\sin\theta_1 + r_1\theta_1\sin\theta_1]\hat{i} + [-r_2\sin\theta_1 + r_1\theta_1\cos\theta_1 - a\cos\theta_1]\hat{k}\}\delta\theta_1$$

$$\delta r_{out}\{[(r_2+c)\cos\theta_1 + r_1\theta_1\sin\theta_1]\hat{i} + [-(r_2+c)\sin\theta_1 + r_1\theta_1\cos\theta_1]\hat{k}\}\delta\theta_1$$

The virtual work for each applied force is simply the dot product of each applied force with its corresponding virtual displacement. $5W''; = F;\cdot 5-r;$. Therefore, 5W;n is expressed in Eq. 15:

$$\delta W_{in} = -F_{in}[-r_2\sin\theta_1 + r_1\theta_1\cos\theta_1 - a\cos\theta_1]\delta\theta_1$$

Interestingly, the expression for ut can be simplified significantly using trigonometric identities until it simply becomes Eq. 16:

$$\delta W_{out} = -F_{out}(r_2+c)\delta\theta_1$$

The sum of these virtual work terms is the total virtual work for the system and is equal to 0. Carrying out this summation and rearranging terms, the mechanical advantage or the ratio $F_{o}/F;n$ is Eq. 17:

$$\frac{F_{out}}{F_{in}} = \frac{(a - r_1\theta_1)\cos\theta_1 + r_2\sin\theta_1}{r_2 + c}$$

Figure 13:
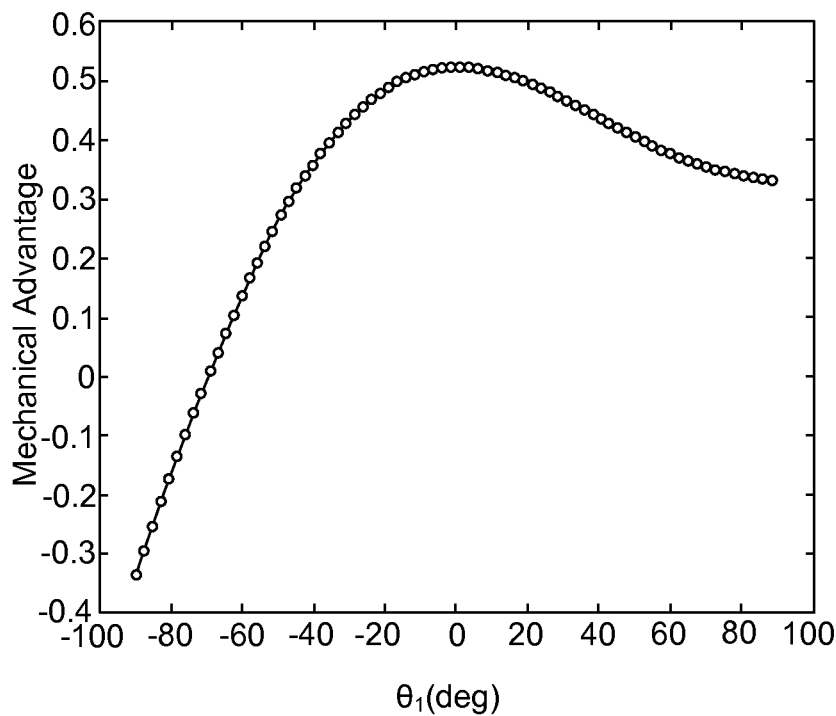
FIG. 13 illustrates a graph depicting the mechanical advantage of the wrist mechanism according to an aspect.

As a check, this planar case was compared with an equivalent system based on the 3D kinematic model derived in Eq. 8. The result can be seen plotted in FIG. 13. FIG. 13 illustrates the mechanical advantage in the x-z plane with a max value of 0.5 and the zero value at −70 degrees according to an aspect. Note that the mechanical advantage does pass through zero. This occurs when the input force passes directly over the point of contact at approximately −60 degrees.

The same process can be followed to derive an expression for the mechanical advantage in the y-z plane. The 3D position equations developed in Eq. 8 are used here to demonstrate the method used previously. The same vector describing the input force as expressed in Eq. 9 can be reused here. The output force however is modeled as a follower force in the rotating coordinate frame in Eq. 18:

$F_{out}' = -F_{out}\hat{j}'|$

This vector can then be transformed into the global coordinate frame in Eq. 19:

$[R]^T F_{out}' = -F_{out}(\sin\theta_1 \sin\theta_2\hat{i} + \cos\theta_2\hat{j} + \cos\theta_1 \sin\theta_2\hat{k})$ The rest of the process follows the same steps taken in the previous section but with the initial position vectors derived from Eq. 8. Accordingly, the location of the input force contains no a or c component, and is expressed in Eq. 20:

$r_{in} = [(r_1 + r_2)\sin\theta_1 - r_1\theta_1\cos\theta_1 + b\sin\theta_1\sin\theta_2]\hat{i} + l_{\|}f \setminus + bC$ $( > S\{\setminus\hat{j} + [(r1 + r\cdot)]C <]s It1 + rt O1 sil1\{\}1 + hCf)S91 sil1\{:\}.\hat{J}k$ Similarly, the vector to the output force has no component of a orb in it as shown by Eq. 21:

$r_{out} = [(r_1+r_2)\sin\theta_1 + r_1\theta_1\cos\theta_1 + c\sin\theta_1\cos\theta_2]\hat{i} - [(r_2\theta_2 + c\sin\theta_2]\hat{j} + [(r_1 r_2)\cos\theta_1 + r_1\theta_1\sin\theta_1 + c\cos\theta_1\cos\theta_2]\hat{k}|$ The derivation of the position vectors described in Eqs. 20-21 is cumbersome and quickly becomes complicated. That is, however, until the planar assumption is applied. Both equations include the term $\delta\theta_1/\delta\theta_2$, or the change of $\theta_1$ with respect to $\theta_2$. As these two separate DoFs are independent of each other, those terms with this relationship equal zero and can be eliminated. When that is done the virtual displacements become Eqs. 22-23:

$\delta r_{in}::::\{\sin\theta_1\cos\theta_2\hat{i} - [r_2 + b\sin\theta_2]\hat{j} + [b\cos\theta_1\cos\theta_2]\hat{k}\}\delta\theta_2|$ $\delta r_{out} = \{[+c\sin\theta_1\sin\theta_2]\hat{i} - [r_2 + c\cos\theta_2]\hat{j} - [c\cos\theta_1\sin\theta_2]\hat{k}\}\delta\theta_2$ The corresponding virtual work is shown in Eqs. 24-25:

$\delta W_{in} = -F_{in}(b\cos\theta_1\cos\theta_2)\delta\theta_2$ $\delta W_{out} = F_{out}[\sin\theta_1\sin\theta_2(c\sin\theta_1\sin\theta_2) + \cos\theta_2(r_2 + c\cos\theta_2) + \cos\theta_1\sin\theta_2(c\cos\theta_1\sin\theta_2)]\delta\theta_2$ Using trigonometric identities, Eq. 25 simplifies conveniently to Eq. 26:

$\delta W_{out} F_{out}[r_2\cos\theta_2 + c]\delta\theta_2|$

Finally, summing the two separate virtual work terms and rearranging, the mechanical advantage in the y-z plane is Eq. 27:

$$\frac{F_{out}}{F_{in}} = \frac{b\cos\theta_1\cos\theta_2}{r_2\cos\theta_2 + c}$$

Figure 14:
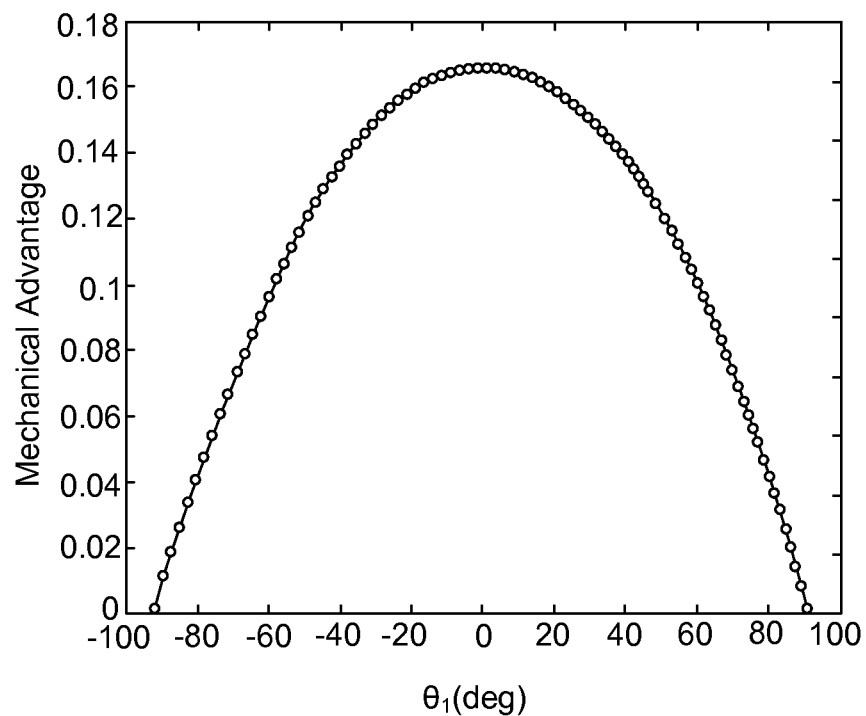
FIG. 14 illustrates a graph depicting the mechanical advantage of the wrist mechanism according to another aspect.

The mechanical advantage for the purely planar case where $\theta_1=0$ can be seen in FIG. 14. For example, FIG. 14 illustrates the mechanical advantage in the y-z plane, where the max value is 0.17 and zeros at plus or minus 90 degrees. Referring to FIGS. 13 and 14, these graphs depict the comparison of the two methods for deriving the mechanical advantage in two orthogonal planes, where the circles and the line represent the 2D and 3D derivations respectively. As the planar and 3D derivations ultimately yield the same equations it is no surprise that they plot the same curve. It is interesting to note that unlike the x-z plane, the mechanical advantage never goes negative in some implementations. It does however approach zero at the extremes of its angular displacement.

Figure 15:
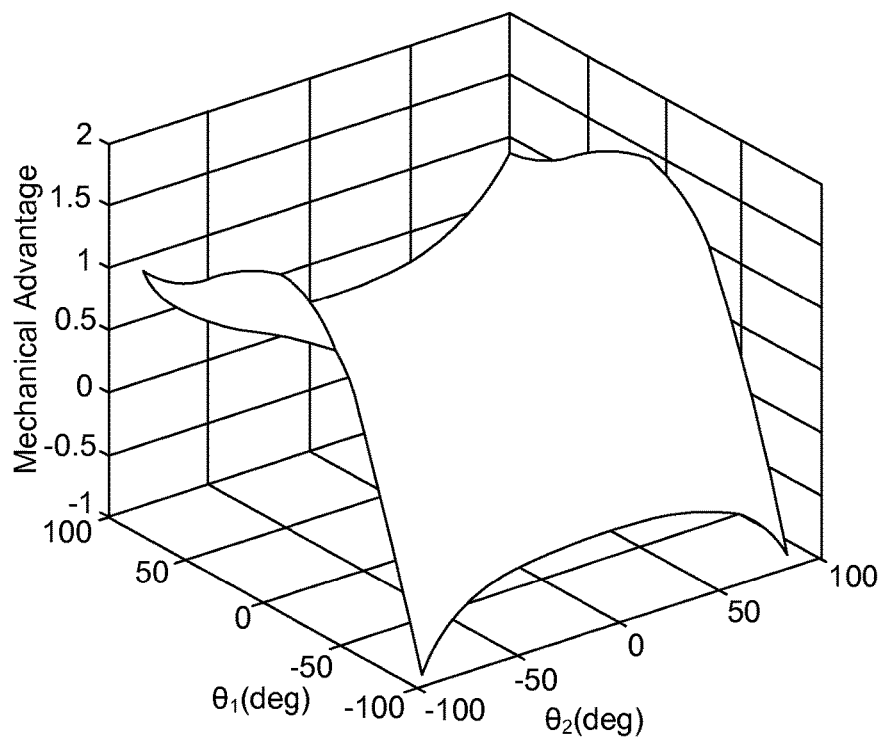
FIG. 15 illustrates a follower force on the wrist mechanism according to an aspect.
Figure 16:
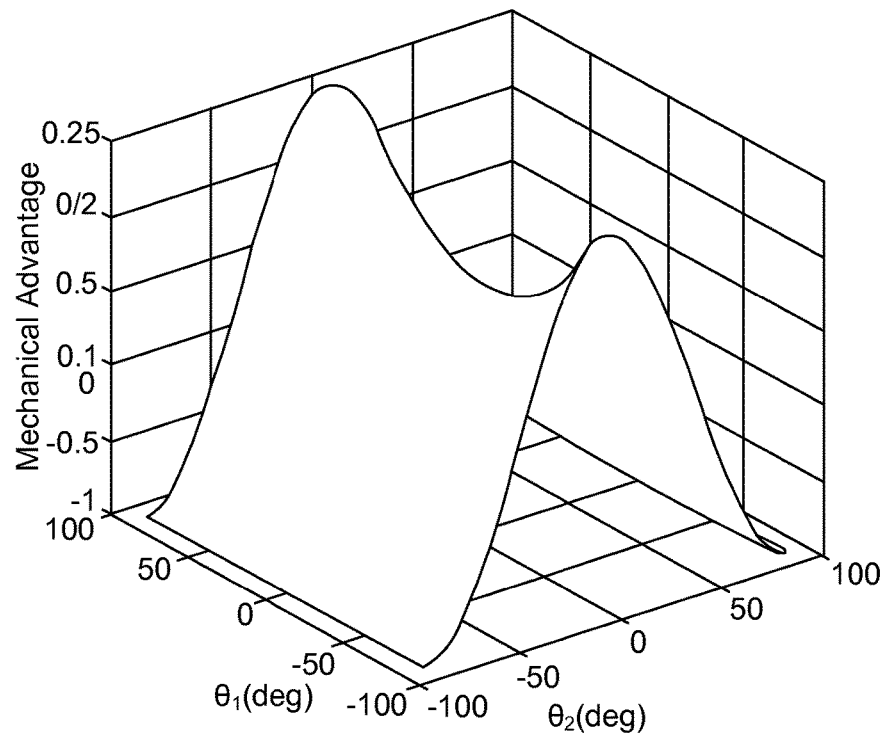
FIG. 16 illustrates a follower force on the wrist mechanism according to another aspect.

FIGS. 15 and 16 show how the 3D derivations of can be used to find the mechanical advantage for these two cases as functions of both $\theta_1$ and $\theta_2$. Eq. 27 is applied where $\theta_1$ is no longer held constant. The result is the surface shown in FIG. 16. An analogous approach is used to produce the surface shown in FIG. 15. FIGS. 15 and 16 illustrate the mechanical advantage for follower forces acting in either the x-z or the y-z planes as both $\theta_1$ and $\theta_2$ vary from plus and minus 90 degrees. FIG. 15 illustrates the follower force in the x-z plane, and FIG. 16 illustrate the follower force in the y-z plane.

While the input-to-output relationships in two dimensions are useful, the relationships in three dimensions can be more practical in some implementations. The illustration in FIG. 17 shows the parameters of interest.

Figure 17:
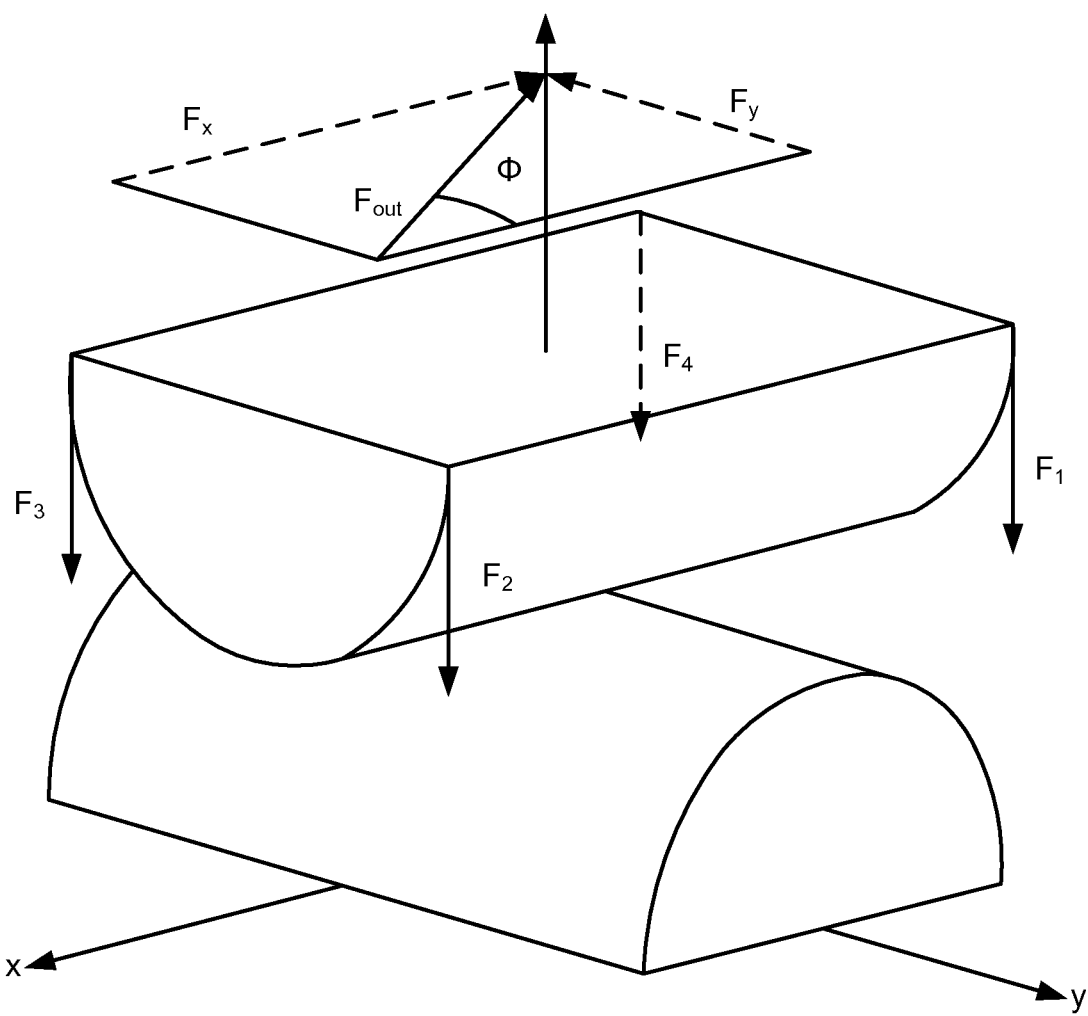
FIG. 17 illustrates a location of input and output forces m three dimensions on the wrist mechanism according to an aspect.

FIG. 17 illustrates a location of input and output forces in three dimensions where $1\setminus$ and FY are components of $F_{;,u_1}$. In FIG. 17, the input forces $P_i-F_3$ are applied at the corners of the platform. The output $F_{;,u_1}$ is a follower force applied at some elevation c above the platform surface. In the neutral position ($\theta_1$ and $\theta_2=0$), it has components in both the x and y directions. As it is body fixed, $F_{;,ut}$ will remain in a plane parallel to the platform surface. Practically, there would be four actuation cables attached to the corners of the platform, however, only three would be providing any resistance against the output at any one time as shown. The angle $\phi$ defines the location between the x-z and y-z planes where the output force acts. For the special cases $\phi=0$ or 90 degrees, the problem simplifies to one of the two planar cases presented previously.

First, the input forces derived for both the planar cases are actually combinations of two forces at the corners of the platform. A single force placed at the center of any side of the mechanism (half way between $F_;$. and $F_;$ or $F_2$ and $F_3$ in FIG. 17) represents the placement of an actuation cable there. This is an infeasible configuration as the base would interfere with the cabling. Therefore, four actuation cables would likely be placed at the corners as shown in FIG. 17. When the crossed cylinders wrist experiences an applied output force with components in both the x-z and y-z planes, there would be opposing forces in three of the four cables.

Figure 18:
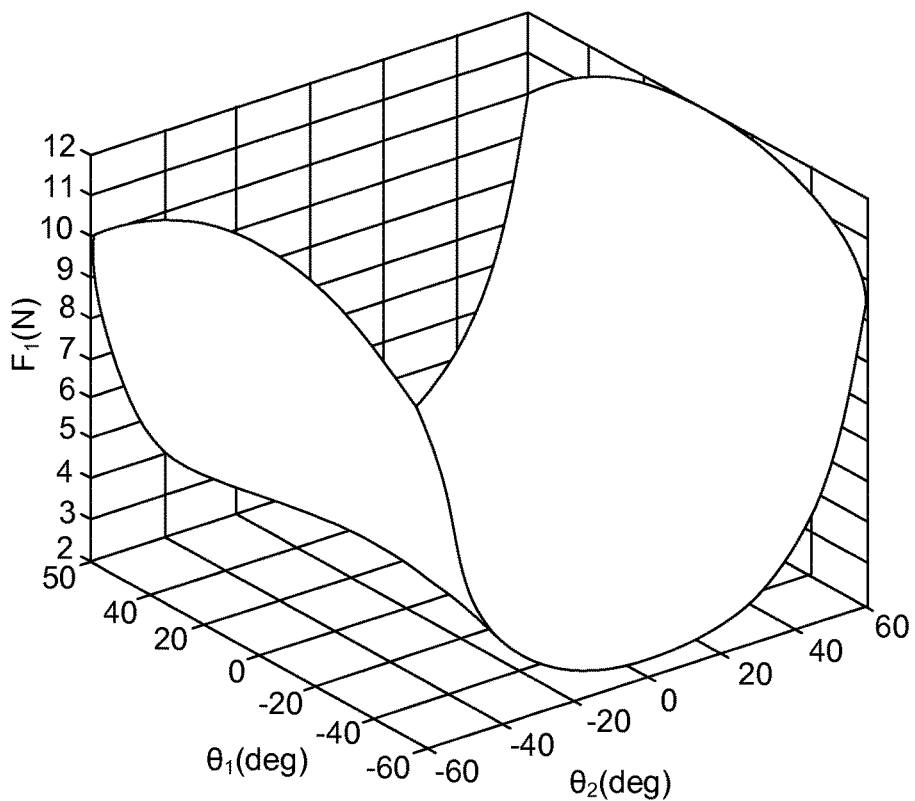
FIG. 18 illustrates a graph of a first force applied to the wrist mechanism according to an aspect.
Figure 19:
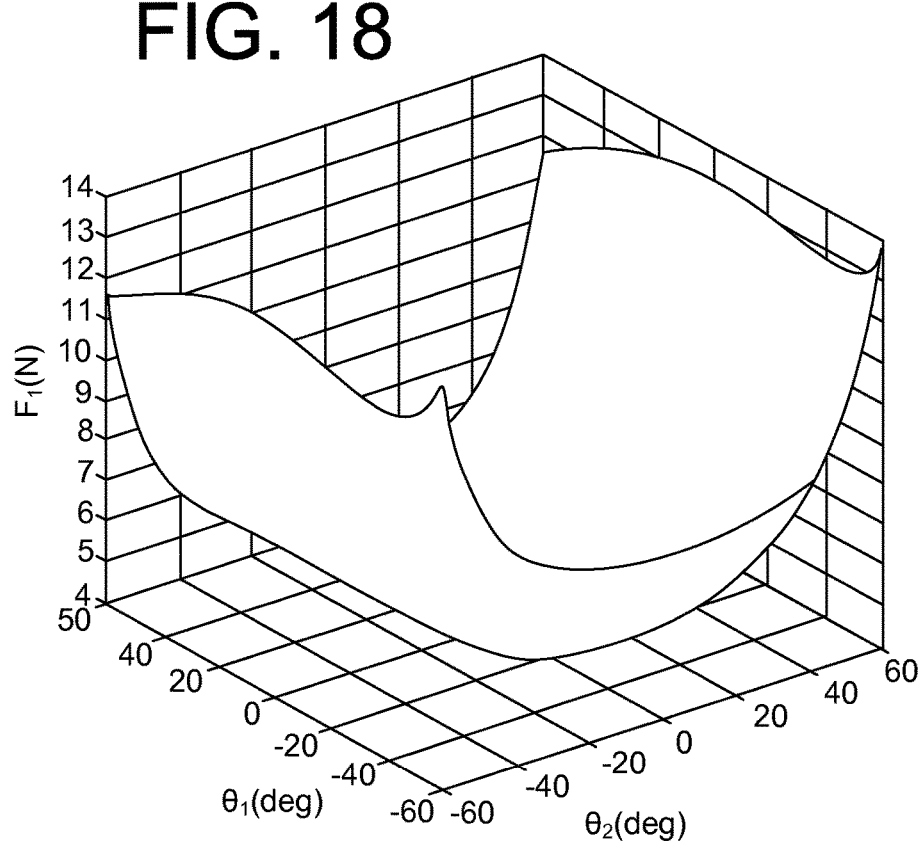
FIG. 19 illustrates a graph of a second force applied to the wrist mechanism according to an aspect.
Figure 20:
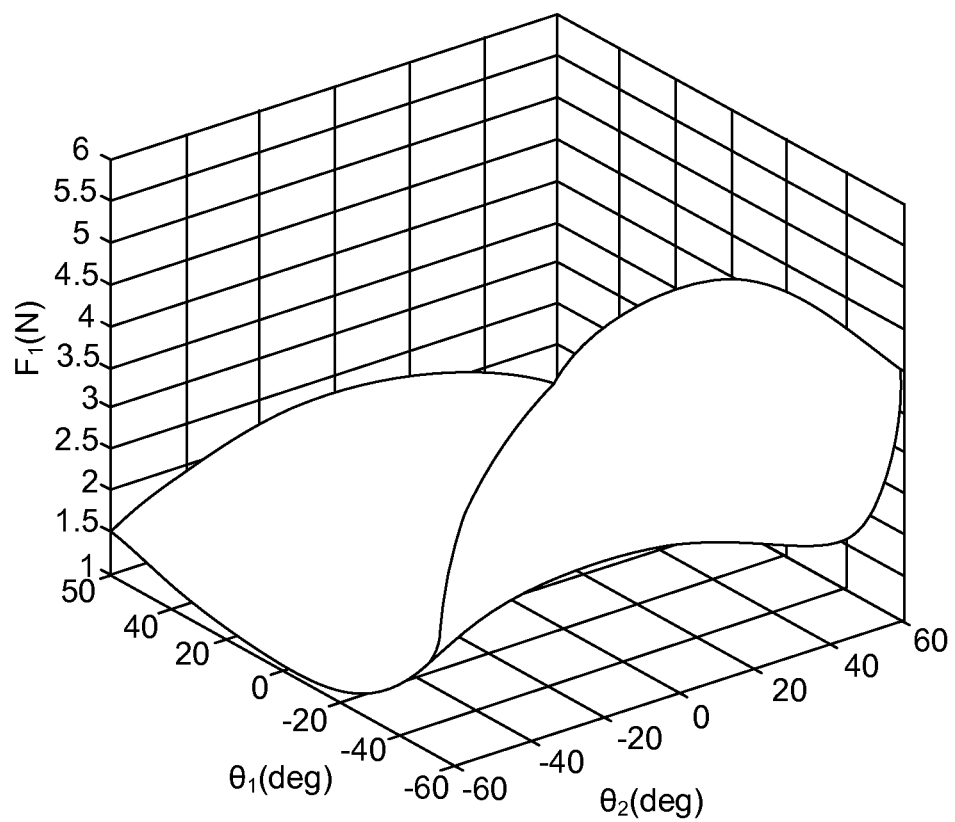
FIG. 20 illustrates a graph of a second force applied to the wrist mechanism according to an aspect.

The three forces corresponding with the engaged cables are shown in FIGS. 18, 19, and 20. FIG. 18 illustrates the force $P_i$ as functions of $\theta_1$ and $\theta_2$ ($F_0=2N$, $\phi=30$ degrees). FIG. 19 illustrates the force $F_2$ as functions of $\theta_1$ and $\theta_2$ ($F_0=2N$, $\phi=30$ degrees). FIG. 20 illustrates the force $F_3$ as functions of $\theta_1$ and $\theta_2$ ($F_0=2N$, $\phi=30$ degrees). The solutions for the planar cases can be combined to solve for the input, or actuation, forces required for a desired output force. As mentioned before, mechanical advantage would be less meaningful in this case because the three cable forces would need to be combined into some fictitious force. For the purpose of illustration, an output force of 2N has been chosen to represent a likely loading condition for a 3 mm instrument. The angle $\phi$ has been set arbitrarily to 30 degrees.

The values for $F_{;n}$ solved for previously are broken down into components and then recombined to arrive at expressions for $F_{;.}$, $F_2$, and $P_{o,}$. When $F_{;n}$ for the x-z plane is divided in two it then equals $PO_{,}$. Similarly, half of $F_{;n}$ for the y-z plane equals Pi. This is due to the symmetry about the center of the joint. $F_2$ is the sum of $F_{;.}$ and Po, as it contributes to both sets of planar motion. The three charts shown in FIGS. 19-21 represent the amount of force applied at each corner to achieve the desired (in this case 2N) output.

The angle ¢ can be varied from 0 to 90 degrees and it will have a predictable impact on the three input forces. As ¢ approaches 0, $F_2$ and Po, increase in magnitude as they will provide more and more of the resistance against the output force. Conversely, F;. and $F_2$ will increase in magnitude as ¢ approaches 90 degrees. Because of symmetry, the results shown here can be applied to any corner of the crossed cylinders wrist. When applied to the corner diagonally across the results will be identical. For the other two corners the positions for F;. and Po, will be switched but the magnitudes will be the same.

It is important to characterize the load carrying capabilities of the gearing in order to define the limits of the mechanism. As the loading conditions deviate far from typical gearing configurations, the problem has been simplified relatively significantly. The approach is to find the maximum load allowable for a single gear tooth in several loading scenarios. This provides a baseline for the magnitude of loads that the mechanism is capable of carrying.

Figure 21:
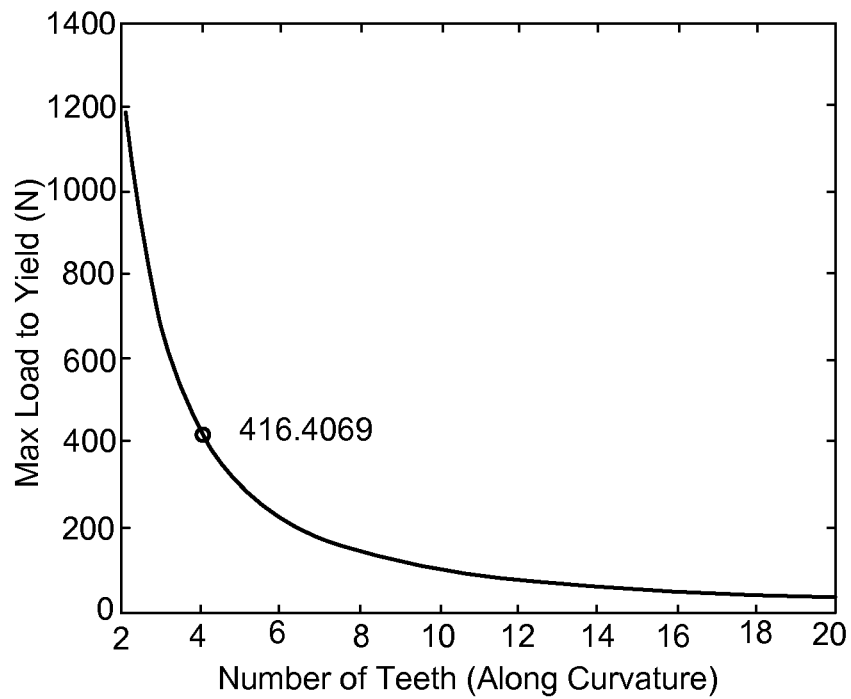
FIG. 21 illustrates a graph of the maximum loads that can be applied to a gear tooth in terms of compression according to an aspect.
Figure 22:
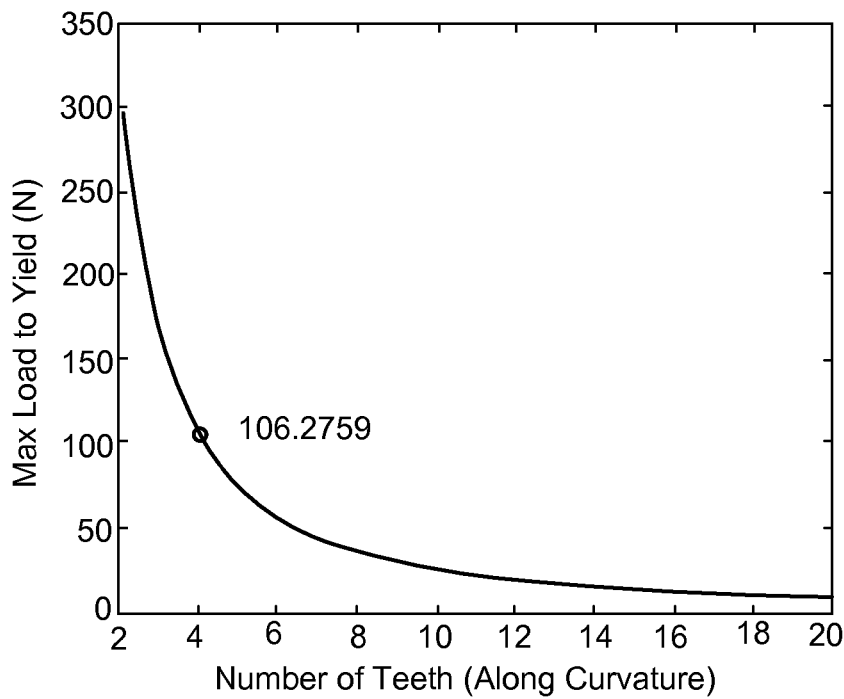
FIG. 22 illustrates a graph of the maximum loads that can be applied to a gear tooth in terms of bending according to an aspect.

FIGS. 21-22 show the maximum loads that can be applied to a single tooth as a function of the number of teeth on the mechanism. FIG. 21 illustrates a graph of the maximum loads that can be applied to a single tooth in terms of compression, and FIG. 22 illustrates a graph of the maximum loads that can be applied to a single tooth in terms of bending. The marker (dot) in each graph indicates the maximum stress for the mechanism as it is currently configured with 4 gear teeth on each row. The compressive load is calculated using the stress over the area (FIG. 21), while the bending stress is derived from the Lewis Bending Equation (FIG. 22). There is an inverse relationship between the number of teeth and the applied load due to the changing cross-sectional area of the individual tooth. Additionally, the load can be adjusted by the contact ratio between the base and the platform. This ratio is the number of teeth that are engaged at a point in time, effectively increasing the load capacity of the mechanism. Using the contact ratio as a scaling factor, FIG. 21 shows that a tooth is capable of a compressive load of 416 N (93.5 lb.) and similarly, and FIG. 22 shows a maximum bending capacity of 106 N (23.8 lb.) for a 4 tooth mechanism.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device comprising:
   a shaft, a wrist mechanism, an end effector, means for applying a first pulling force, and means for applying a second pulling force;
   the wrist mechanism comprising a first cylinder portion and a second cylinder portion, the first cylinder portion being coupled to the end effector, the second cylinder portion being coupled to the shaft, the first cylinder portion comprising an outer surface that is a first partial cylinder, the second cylinder portion comprising an outer surface that is a second partial cylinder, and a longitudinal axis being defined for the second cylinder portion;
   the means for applying the first pulling force pulling the first cylinder portion to roll the first partial cylinder along the second partial cylinder in a direction parallel to the longitudinal axis of the second cylinder portion; and
   the means for applying the second pulling force pulling the first cylinder portion to roll the first partial cylinder along the second partial cylinder in a direction around the longitudinal axis of the second cylinder portion,
   wherein the outer surface of the first cylinder portion comprises first teeth, the first teeth each comprising a rack profile in a direction parallel to a longitudinal axis of the first cylinder portion and an involute profile in a direction around the longitudinal axis of the first cylinder portion.

2. The medical device of claim 1, wherein the outer surface of the second cylinder portion comprises second teeth each comprising a third profile shaped to engage the rack profile of the first teeth and a fourth profile shaped to engage the involute profile of the first teeth.

3. The medical device of claim 1, wherein the first cylinder portion comprises a first plurality of sheets.

4. The medical device of claim 3, wherein the first plurality of sheets comprises the first teeth.

5. The medical device of claim 4, wherein the second cylinder portion comprises a second plurality of sheets, the second plurality of sheets comprising second teeth engaged with the first teeth of the first plurality of sheets.

6. The medical device of claim 1, wherein the means for applying the first pulling force and the means for applying the second pulling force ensure the first partial cylinder stays rollably engaged with the second partial cylinder while actuating the rolling of the first partial cylinder along the second partial cylinder.

7. The medical device of claim 1, wherein the outer surface of the second cylinder portion comprises second teeth, the second teeth each comprising the rack profile in a direction parallel to a longitudinal axis of the second cylinder portion and the involute profile in the direction around the longitudinal axis of the second cylinder portion.

8. The medical device of claim 1, wherein the means for applying the first pulling force comprises a first pair of actuation cables and the means for applying the second pulling force comprises a second pair of actuation cables.

9. The medical device of claim 8, wherein each actuation cable of the first and second pairs of actuation cables is attached to a respective corner of the first cylinder portion.

10. The medical device of claim 1, wherein the longitudinal axis of the second cylinder portion is orthogonal to a longitudinal axis of the first cylinder portion.

11. The medical device of claim 1, wherein concurrently actuating the means for applying the first pulling force and the means for applying the second pulling force concurrently causes: (i) the first partial cylinder to roll along the second partial cylinder in a direction parallel to the longitudinal axis of the second cylinder portion, and (ii) the first partial cylinder to roll along the second partial cylinder in a direction around the longitudinal axis of the second cylinder portion.

12. A medical device comprising:
   a shaft, a wrist mechanism, an end effector, means for applying a first pulling force, and means for applying a second pulling force;
   the wrist mechanism comprising a first cylinder portion and a second cylinder portion, the first cylinder portion being coupled to the end effector, the second cylinder portion being coupled to the shaft, the first cylinder portion comprising an outer surface that is a first partial cylinder, the second cylinder portion comprising an outer surface that is a second partial cylinder, and a longitudinal axis being defined for the second cylinder portion;

the means for applying the first pulling force pulling the first cylinder portion to roll the first partial cylinder along the second partial cylinder in a direction parallel to the longitudinal axis of the second cylinder portion; and the means for applying the second pulling force pulling the first cylinder portion to roll the first partial cylinder along the second partial cylinder in a direction around the longitudinal axis of the second cylinder portion, wherein the means for applying the first pulling force comprises a first pair of actuation cables and the means for applying the second pulling force comprises a second pair of actuation cables, and wherein each actuation cable of the first and second pairs of actuation cables is attached to a respective corner of the first cylinder portion.

13. The medical device of claim 12, wherein the outer surface of the first cylinder portion comprises first teeth, and wherein the first teeth each comprise a first profile in a direction parallel to a longitudinal axis of the first cylinder portion and a second profile in a direction around the longitudinal axis of the first cylinder portion, the second profile being different from the first profile.

14. The medical device of claim 13, wherein the outer surface of the second cylinder portion comprises second teeth each comprising a third profile shaped to engage the first profile of the first teeth and a fourth profile shaped to engage the second profile of the first teeth.

15. The medical device of claim 12, wherein the outer surface of the first cylinder portion comprises first teeth, and the outer surface of the second cylinder portion comprises second teeth engaged with the first teeth.

16. The medical device of claim 12, wherein the first cylinder portion comprises a first plurality of sheets, and wherein the first plurality of sheets comprises first teeth.

17. The medical device of claim 16, wherein the second cylinder portion comprises a second plurality of sheets, the second plurality of sheets comprising second teeth engaged with the first teeth of the first plurality of sheets.

18. The medical device of claim 12, wherein the means for applying the first pulling force and the means for applying the second pulling force ensure the first partial cylinder stays rollably engaged with the second partial cylinder while actuating the rolling of the first partial cylinder along the second partial cylinder.

19. The medical device of claim 12, wherein the outer surface of the first cylinder portion comprises first teeth, the first teeth each comprising a rack profile in a direction parallel to a longitudinal axis of the first cylinder portion and an involute profile in a direction around the longitudinal axis of the first cylinder portion, and wherein the outer surface of the second cylinder portion comprises second teeth, the second teeth each comprising the rack profile in a direction parallel to a longitudinal axis of the second cylinder portion and the involute profile in the direction around the longitudinal axis of the second cylinder portion.

20. The medical device of claim 12, wherein the longitudinal axis of the second cylinder portion is orthogonal to a longitudinal axis of the first cylinder portion, and wherein concurrently actuating the means for applying the first pulling force and the means for applying the second pulling force concurrently causes: (i) the first partial cylinder to roll along the second partial cylinder in a direction parallel to the longitudinal axis of the second cylinder portion, and (ii) the first partial cylinder to roll along the second partial cylinder in a direction around the longitudinal axis of the second cylinder portion.

* * * * *